(12) United States Patent
Gustavson et al.

(10) Patent No.: US 8,497,080 B2
(45) Date of Patent: Jul. 30, 2013

(54) METHODS FOR DETERMINING SIGNAL TRANSDUCTION ACTIVITY IN TUMORS

(71) Applicant: HistoRx, Inc., New Haven, CT (US)

(72) Inventors: Mark Gustavson, Niantic, CT (US); Jennifer Giltnane, Nashville, TN (US); Marisa P. Dolled-Filhart, New Haven, CT (US); Robert L. Camp, San Francisco, CA (US); David L. Rimm, Branford, CT (US)

(73) Assignees: HistoRx, Inc., New Haven, CT (US); Yale University, New Haven, CT (US)

( * ) Notice: Subject to any disclaimer, the term of this patent is extended or adjusted under 35 U.S.C. 154(b) by 0 days.

(21) Appl. No.: 13/759,765

(22) Filed: Feb. 5, 2013

(65) Prior Publication Data

US 2013/0143763 A1 Jun. 6, 2013

Related U.S. Application Data

(62) Division of application No. 12/299,699, filed as application No. PCT/US2007/011052 on May 7, 2007, now Pat. No. 8,367,351.

(60) Provisional application No. 60/797,932, filed on May 6, 2006.

(51) Int. Cl.
  *G01N 31/00* (2006.01)
  *G01N 33/53* (2006.01)

(52) U.S. Cl.
  USPC ............ 435/7.21; 435/7.1; 436/1; 436/8; 436/501; 436/518; 424/9.1; 424/520; 530/300; 530/350

(58) Field of Classification Search
  None
  See application file for complete search history.

(56) References Cited

U.S. PATENT DOCUMENTS

| | | | |
|---|---|---|---|
| 4,998,284 A | 3/1991 | Bacus et al. | |
| 5,386,819 A | 2/1995 | Kaneko et al. | |
| 5,784,162 A | 7/1998 | Cabib et al. | |
| 5,989,835 A | 11/1999 | Dunlay et al. | |
| 5,998,151 A | 12/1999 | Johnston et al. | |
| 6,026,174 A | 2/2000 | Palcic et al. | |
| 6,151,405 A | 11/2000 | Douglass et al. | |
| 6,165,734 A | 12/2000 | Garini et al. | |
| 6,215,892 B1 | 4/2001 | Douglass et al. | |
| 6,229,649 B1 | 5/2001 | Woods et al. | |
| 6,251,601 B1 | 6/2001 | Bao et al. | |
| 6,337,472 B1 | 1/2002 | Garner et al. | |
| 6,466,690 B2 | 10/2002 | Bacus et al. | |
| 6,727,071 B1 | 4/2004 | Dunlay et al. | |
| 7,050,087 B2 | 5/2006 | Harari et al. | |
| 7,709,222 B2 | 5/2010 | Rimm et al. | |
| 7,873,480 B2 | 1/2011 | Rimm et al. | |
| 8,036,833 B2 | 10/2011 | Rimm | |
| 8,121,794 B2 | 2/2012 | Rimm | |
| 8,185,320 B2 | 5/2012 | Rimm | |
| 2002/0094956 A1 | 7/2002 | Cosgrove | |
| 2003/0036855 A1 | 2/2003 | Harris et al. | |
| 2005/0227303 A1 | 10/2005 | Guo et al. | |
| 2006/0127928 A1 | 6/2006 | Bacus et al. | |
| 2006/0147959 A1 | 7/2006 | Bell et al. | |
| 2006/0275844 A1 | 12/2006 | Linke et al. | |
| 2008/0026415 A1 | 1/2008 | Rimm et al. | |
| 2009/0155767 A1 | 6/2009 | Rimm et al. | |
| 2009/0155842 A1 | 6/2009 | Bakk et al. | |
| 2010/0240035 A1 | 9/2010 | Jablons | |
| 2011/0081665 A1 | 4/2011 | Rimm et al. | |

FOREIGN PATENT DOCUMENTS

| | | |
|---|---|---|
| WO | WO 90/10276 | 9/1990 |
| WO | WO 97/04418 | 2/1997 |
| WO | WO 97/22848 | 6/1997 |
| WO | WO 99/47963 | 9/1999 |
| WO | WO 00/24940 | 5/2000 |
| WO | WO 00/31534 | 6/2000 |
| WO | WO 00/62247 | 10/2000 |
| WO | WO 01/20044 | 3/2001 |
| WO | WO 01/22086 | 3/2001 |
| WO | WO/02/86498 | 4/2002 |
| WO | WO 03/012067 | 2/2003 |
| WO | WO 2008/008500 | 1/2008 |
| WO | WO 2009/005715 | 1/2009 |
| WO | WO 2009/005816 | 1/2009 |
| WO | WO 2011/047109 | 4/2011 |
| WO | WO 2011/053823 | 5/2011 |
| WO | PCT/US2012/026201 | 2/2012 |

OTHER PUBLICATIONS

International Search Report issued by the International Searching Authority in connection with International Application No. PCT/US2002/012084.

International Preliminary Examination Report issued by the International Bureau in connection with International Application No. PCT/US2002/012084.

Pending claims for U.S. Appl. No. 12/215,458, filed Jun. 27, 2008.

(Continued)

Primary Examiner — Lisa Cook
(74) Attorney, Agent, or Firm — John P. White; Cooper & Dunham LLP (57) ABSTRACT

The method of the invention pertains to determining signal transduction activity in a tissue section by immunohistochemistry techniques. The expression level of the receptor of interest is determined as well as the expression levels of one or more effector molecules of the receptor signal transduction pathway. Furthermore a combined ratio of expression levels of effector molecules in subcellular compartments with the receptor expression was found to have prognostic significance.

12 Claims, 5 Drawing Sheets

OTHER PUBLICATIONS

Dec. 18, 2003 Office Action issued in connection with U.S. Appl. No. 10/062,308, filed Feb. 1, 2002, now U.S. Patent No. 7,219,016.
Jun. 16, 2004 Office Action issued in connection with U.S. Appl. No. 10/062,308, filed Feb. 1, 2002, now U.S. Patent No. 7,219,016.
Apr. 7, 2005 Office Action issued in connection with U.S. Appl. No. 10/062,308, filed Feb. 1, 2002, now U.S. Patent No. 7,219,016.
Oct. 19, 2005 Office Action issued in connection with U.S. Appl. No. 10/062,308, filed Feb. 1, 2002, now U.S. Patent No. 7,219,016.
Apr. 27, 2006 Office Action issued in connection with U.S. Appl. No. 10/062,308, filed Feb. 1, 2002, now U.S. Patent No. 7,219,016.
Nov. 24, 2006 Office Action issued in connection with U.S. Appl. No. 10/062,308, filed Feb. 1, 2002, now U.S. Patent No. 7,219,016.
Mar. 2, 2004 Response to Dec. 18, 2003 Office Action issued in connection with U.S. Appl. No. 10/062,308 filed Feb. 1, 2002, now U.S. Patent No. 7,219,016.
Sep. 20, 2004 Response to Jun. 16, 2004 Office Action issued in connection with U.S. Appl. No. 10/062,308, filed Feb. 1, 2002, now U.S. Patent No. 7,219,016.
Jun. 30, 2005 Response to Apr. 7, 2005 Office Action issued in connection with U.S. Appl. No. 10/062,308, filed Feb. 1, 2002, now U.S. Patent No. 7,219,016.
Feb. 6, 2006 Response to Oct. 19, 2005 Office Action issued in connection with U.S. Appl. No. 10/062,308, filed Feb. 1, 2002, now U.S. Patent No. 7,219,016 (Exhibit 14).
Aug. 28, 2006 Response to Apr. 27, 2006 Office Action issued in connection with U.S. Appl. No. 10/062,308, filed Feb. 1, 2002, now U.S. Patent No. 7,219,016.
Jan. 24, 2007 Response to Nov. 24, 2006 Office Action issued in connection with U.S. Appl. No. 10/062,308, filed Feb. 1, 2002, now U.S. Patent No. 7,219,016.
Jan. 13, 2010 Office Action issued in connection with U.S. Appl. No. 11/789,361, filed Apr. 23, 2007.
Feb. 16, 2010 Response to Jan. 13, 2010 Office Action issued in connection with U.S. Appl. No. 11/789,361, filed Apr. 23, 2007.
May 27, 2010 Office Action issued in connection with U.S. Appl. No. 11/789,361, filed Apr. 23, 2007.
Aug. 27, 2010 Response to May 27, 2010 Office Action issued in connection with U.S. Appl. No. 11/789,361, filed Apr. 23, 2007.
Feb. 19, 2010 Office Action issued in connection with U.S. Appl. No. 11/894,297, filed Aug. 20, 2007.
Mar. 26, 2010 Response to Feb. 19, 2010 Office Action issued in connection with U.S. Appl. No. 11/894,297, filed Aug. 20, 2007.
Jun. 22, 2010 Office Action issued in connection with U.S. Appl. No. 11/894,297, filed Aug. 20, 2007.
Sep. 22, 2010 Response to Jun. 22, 2010 Office Action issued in connection with U.S. Appl. No. 11/820,786, filed Jun. 20, 2007.
Sep. 22, 2010 Response to Jun. 22, 2010 Office Action issued in connection with U.S. Appl. No. 11/894,297, filed Aug. 20, 2007.
Mar. 1, 2010 Office Action issued in connection with U.S. Appl. No. 11/894,680, filed Aug. 20, 2007.
Jun. 22, 2010 Office Action issued in connection with U.S. Appl. No. 11/820,786.
Jun. 1, 2010 Response to Mar. 1, 2010 Office Action issued in connection with U.S. Appl. No. 11/894,680, filed Aug. 20, 2007.
Supplemental European Search report issued by European Patent Office in connection with International Application No. PCT/US2002/012084.
Agard D A, "Optical Sectioning Microscopy: Cellular Architecture in Three Dimensions," Annual Review of Biophysics and Bioengineering, Annual Reviews Inc., vol. 13, Jan. 1, 1984, pp. 191-219.
Official Communication Pursuant to Article 94(3) from European Patent Office dated Oct. 1, 2009 in connection with European Patent Application No. 02739157.2 (national stage of PCT International Application No. PCT/US02/12084).
Feb. 11, 2010 Response to the Official Communication Pursuant to Article 94(3) from European Patent Office issued Oct. 1, 2009 in connection with European Patent Application No. 02739157.2 (national stage of PCT International Application No. PCT/US02/12084).
Examiner's Report issued Nov. 15, 2006 by the Australian Patent Office in connection with Australian Patent Application No. 2002311827, now Australian Patent No. 2002311827 (national stage of PCT International Application No. PCT/US02/12084).
Jul. 15, 2008 Response to the Examiner's Report issued Nov. 15, 2006 by the Australian Patent Office in connection with Australian Patent Application No. 2002311827, now Australian Patent No. 2002311827 (national stage of PCT International Application No. PCT/US02/12084).
Office Action issued Oct. 20, 2009 by the Canadian Patent Office in connection with Canadian Patent Application No. 2442604 (national stage of PCT International Application No. PCT/US02/12084).
Apr. 20, 2010 Response to the Office Action issued Oct. 20, 2009 by the Canadian Patent Office in connection with Canadian Patent Application No. 2442604 (national stage of PCT International Application No. PCT/US02/12084).
English translation of Official Action issued Jul. 4, 2007 by the Japanese Patent Office in connection with Japanese Patent Application No. 2002-583976 (national stage of PCT International Application No. PCT/US02/12084).
English translation of Official Action issued May 19, 2008 by the Japanese Patent Office in connection with Japanese Patent Application No. 2002-583976 (national stage of PCT International Application No. PCT/US02/12084).
English translation of Official Action issued Apr. 10, 2009 by the Japanese Patent Office in connection with Japanese Patent Application No. 2002-583976 (national stage of PCT International Application No. PCT/US02/12084).
Jan. 4, 2008 Response to Japanese Official Action issued issued Jul. 4, 2007 by the Japanese Patent Office in connection with Japanese Patent Application No. 2002-583976 and English translation of the amended claims (national stage of PCT International Application No. PCT/US02/12084).
Oct. 7, 2008 Response to Japanese Official Action issued issued May 19, 2008 by the Japanese Patent Office in connection with Japanese Patent Application No. 2002-583976 and Englisht translation of the amended claims (national stage of PCT International Application No. PCT/US02/12084).
Aug. 17, 2009 Response to Japanese Official Action issued issued Apr. 10, 2009 by the Japanese Patent Office in connection with Japanese Patent Application No. 2002-583976 (national stage of PCT International Application No. PCT/US02/12084).
Santi DV. "The mechanism and structure of thymidylate synthetase," Nucleic Acids Symp Ser 1986(17):125-6.
Berger SH, Berger FG. "Thymidylate synthase as a determinant of 5-fluoro-2'-deoxyuridine response in human colonic tumor cell lines," Mol Pharmacol 1988;34(4):474-9.
Johnston PG, Drake JC, Trepel J, Allegra CJ. "Immunological quantitation of thymidylate synthase using the monoclonal antibody TS 106 in 5-fluorouracil-sensitive and -resistant human cancer cell lines," Cancer Res 1992;52(16):4306-12.
Johnston PG, Lenz HJ, Leichman CG, Danenberg KD, Allegra CJ, Danenberg PV, et al. "Thymidylate synthase gene and protein expression correlate and are associated with response to 5-fluorouracil in human colorectal and gastric tumors," Cancer Res 1995;55(7):1407-12.
Leichman CG, Lenz HJ, Leichman L, Danenberg K, Baranda J, Groshen S, et al. "Quantitation of intratumoral thymidylate synthase expression predicts for disseminated colorectal cancer responde and resistance to protracted-infusion fluorouracil and weekly leucovorin," J CLin Oncol 1997;15(10):3223-9.
Edler D, Glimelius B, Hallstrom M, Jakobsen A, Johnston PG, Magnusson I, et al. "Thymidylate synthase expression in colorectal cancer: a prognostic and predictive marker of benefit from adjuvant fluorouracil-based chemotherapy," J Clin Oncol 2002;20(7):1721-8.
Edler D, Kressner U, Ragnhammar P, Johnston PG, Magnusson I. Glimelius B, et al. "Immunohistochemically detected thymidylate synthase in colorectal cancer: an independent prognostic factor of survival," Clin Cancer Res 2000;6(2):488-92.
Aschele C, Lonardi S, Monfardini S. "Thymidylate Synthase expression as a predictor of clinical response to fluoropyrimidine-based chemotherapy in advanced colorectal cancer," Cancer Treat Rev 2002;28(1):27-47.

Popat S, Matakidou A, Houlston RS. "Thymidylate synthase expression and prognosis in colorectal cancer: a systematic review and meta-analysis," J Clin Oncol 2004;22(3):529-36.

Leichman CG. "Thymidylate synthase as a predictor of response," Oncology (Williston Park) 1998;12(8 Suppl 6):43-7.

Leichman L, Lenz HJ, Leichman CG, Groshen S, Danenberg K, Baranda J, et al. "Quantitation of intratumoral thymidylate synthase expression predicts for resistance to protracted infusion of 5-fluorouracil and weekly leucovorin in disseminated colorectal cancers: preliminary report from an ongoing trial," Eur J Cancer 1995;31A (7-8) :1306-10.

Liu J, Schmitz JC, Lin X, Tai N, Yan W, Farrell M, et al. "Thymidylate synthase as a translational regulator of cellular gene expression," Biochim Biophys Acta 2002;1587(2-3):174-82.

McCabe A, Dolled-Filhart M, Camp RL, Rimm DL. "Automated quantitative analysis (AQUA) of in situ protein expression, antibody concentration, and prognosis," J Natl Cancer Inst 2005;97:1808-15.

Berger AJ, Kluger HM, Li N, Kielhorn E, Halaban R, Ronai Z, et al. "Subcellular localization of activating transcription factor 2 in melanoma specimens predicts patient survival," 25. Cancer Res. 2003;63(23):8103-8107.

Rimm DL, Camp RL, Charette LA, Costa J, Olsen DA, Reiss M. "Tissue microarray: a new technology for amplification of tissue resources," Cancer J. 2001;7(1):24-31.

Rimm DL, Camp RL, Charette LA, Olsen DA, Provost E. "Amplification of tissue by construction of tissue microarrays," Exp Mol Pathol 2001;70(3):255-64.

Giltnane JM, Rimm DL. "Technology insight: Identification of biomarkers with tissue microarray technology," Nat Clin Pract Oncol 2004;1(2):104-11.

Camp RL, Dolled-Filhart M, Rimm DL. "X-tile: a new bio-informatics tool for biomarker assessment and outcome-based cut-point optimization," 9. Clin. Cancer Res. 2004;10(21):7252-7259.

Raeside DE. "Monte Carlo principles and applications," Phys Med Biol 1976;21(2):181-97.

Camp RL, Charette LA, Rimm DL. "Validation of tissue microarray technology in breast carcinoma," 50. Lab Invest 2000;80(12):1943-1949.

Kucera R, Paulus H. "Localization of the deoxyribonucleotide biosynthetic enzymes ribonucleotide reductase and thymidylate synthase in mouse L cells," Exp Cell Res 1986;167(2):417-28.

Johnston PG, Liang CM, Henry S, Chabner BA, Allegra CJ. "Production and characterization of monoclonal antibodies that localize human thymidylate synthase in the cytoplasm of human cells and tissue," Cancer Res 1991;51(24):6668-76.

Bissoon-Haqqani S, Moyana T, Jonker D, Maroun JA, Birnboim HC. "Nuclear expression of thymidylate synthase in colorectal cancer cell lines and clinical samples," J Histochem Cytochem 2006;54(1):19-29.

Wong NA, Brett L, Stewart M, Leitch A, Longley DB, Dunlop MG, et al. "Nuclear thymidylate synthase expression, p53 expression and 5FU response in colorectal carcinoma," Br J Cancer 2001;85(12):1937-43.

International Preliminary Report on Patentability issued by the International Bureau in connection with International Application No. PCT/US2007/016014.

Written Opinion of the International Searching Authority issued by the International Searching Authority (ISA/US) in connection with International Application No. PCT/US2007/016014.

International Search Report issued by the International Bureau in connection with International Application No. PCT/US2007/016014.

Cascinue S. et al., "Thymidylate synthase protein expression in advanced colon cancer: correlation with the site of metastasis and the clinical response to Leucovorin-modulated bolus 5-fluorouracil," Clinical Cancer Research, Aug. 1999, vol. 5, pp. 1996-1999.

Santini D. et al. "Thymidylate synthase expression in normal colonic mucosa: a predictive marker of toxicity in colorectal cancer patients receiving 5-fluorouracil-based adjuvant chemotherapy," Oncology, 2004, vol. 67, pp. 135-142.

Apr. 8, 2009 Response to the Official Communication Pursuant to Rules 161 and 162 issued by the European Patent Office in connection with European Patent Application No. 07810453.6 (national stage of PCT International Application No. PCT/US07/016014).

International Preliminary Report on Patentability issued by the International Bureau in connection with International Application No. PCT/US2008/08229.

International Preliminary Report on Patentability issued by the International Bureau in connection with International Application No. PCT/US2008/08007.

Tamoxifen for early breast cancer: an overview of the randomised trials, Early Breast Cancer Trialists' Collaborative Group, Lancet, 351:1451-67, 1998.

Dowsett M, Houghton J, Iden C, et al. "Benefit from adjuvant tamoxifen therapy in primary breast cancer patients according oestrogen receptor, progesterone receptor, EGF receptor and HER2 status," Ann Oncol 17:818-26, 2006.

Arpino G, Green SJ, Allred DC, et al. "HER-2 amplification, HER-1 expression, and tamoxifen response in estrogen receptor-positive metastatic breast cancer: a southwest oncology group study." Clin Cancer Res 10:5670-6, 2004.

Arpino G, Weiss H, Lee AV, et al. "Estrogen receptor-positive, progesterone receptor-negative breast cancer: association with growth factor receptor expression and tamoxifen resistance," J Natl Cancer Inst 97:1254-61, 2005.

Linke SP, Bremer TM, Herold CD, et al. "A multimarker model to predict outcome in tamoxifen-treated breast cancer patients," Clin Cancer Res 12:1175-83, 2006.

Osborne CK, Shou J, Massarweh S, et al. "Crosstalk between estrogen receptor and growth factor receptor pathways as a cause for endocrine therapy resistance in breast cancer," Clin Cancer Res 11:865s-70s, 2005.

Osborne CK. "Tamoxifen in the treatment of breast cancer," N Engl J Med 339:1609-18, 1998.

Johnston SR. "Clinical efforts to combine endocrine agents with targeted therapies against epidermal growth factor receptor/human epidermal growth factor receptor 2 and mammalian target of rapamycin in breast cancer," Clin Cancer Res 12:1061s-1068s, 2006.

Schlessinger J. "Cell signaling by receptor tyrosine kinases," Cell 103:211-25, 2000.

Nicholson RI, McClelland RA, Gee JM, et al. "Epidermal growth factor receptor expression in breast cancer: association with response to endocrine therapy," Breast Cancer Res Treat 29:117-25, 1994.

Nicholson RI, McClelland RA, Finlay P, et al. "Relationship between EGF-R, c-erbB-2 protein expression and Ki67 immunostaining in breast cancer and hormone sensitivity," Eur J Cancer 29A:1018-23, 1993.

Gee JM, Robertson JF, Gutteridge E, et al. "Epidermal growth factor receptor/HER2/insulin-like growth factor receptor signalling and oestrogen receptor activity in clinical breast cancer," Endocr Relat Cancer 12 Suppl 1:S99-S111, 2005.

Camp RL, Chung GG, Rimm DL. "Automated subcellular localization and quantification of protein expression in tissue microarrays," Nat Med 8:1323-7, 2002.

McCabe A, Dolled-Filhart M, Camp RL, et al. "Automated quantitative analysis (AQUA) of in situ protein expression, antibody concentration, and prognosis," J Natl Cancer Inst 97:1808-15, 2005.

Ryden L, Jonsson PE, Chebil G, et al. "Two years of adjuvant tamoxifen in premenopausal patients with breast cancer: a randomised, controlled trial with long-term follow-up," Eur J Cancer 41:256-64, 2005.

Ryden L, Jirstrom K, Bendahl P-O, et al. "Tumor-specific expression of vascular endothelial growth factor receptor 2 but not vascular endothelial growth factor or human epidermal growth factor receptor 2 is associated with impaired response to adjuvant tamoxifen in premenopausal breast cancer," J Clin Oncol 23:4695-4704, 2005.

Christensen TA, Reiter JL, Baron AT, et al. "Generation and characterization of polyclonal antibodies specific for human p110 sEGFR," Hybrid Hybridomics 21:183-9, 2002.

Dolled-Filhart M, McCabe A, Giltnane J, et al. "Quantitative in situ analysis of beta-catenin expression in breast cancer shows decreased expression is associated with poor outcome," Cancer Res 66:5487-94, 2006.

Rubin MA, Zerkowski MP, Camp RL, et al. "Quantitative determination of expression of the prostate cancer protein alpha-methylacyl- CoA racemase using automated quantitative analysis (AQUA): a novel paradigm for automated and continuous biomarker measurements," Am J Pathol 164:831-40, 2004.
Jonat W, Pritchard KI, Sainsbury R, et al. "Trends in endocrine therapy and chemotherapy for early breast cancer: a focus on the premenopausal patient," J Cancer Res Clin Oncol 132:275-86, 2006.
Reiter JL, Maihle NJ. "Characterization and expression of novel 60-kDa and 110-kDa EGFR isoforms in human placenta," Ann N Y Acad Sci 995:39-47, 2003.
Schiff R, Massarweh SA, Shou J, et al. "Advanced concepts in estrogen receptor biology and breast cancer endocrine resistance: implicated role of growth factor signaling and estrogen receptor coregulators," Cancer Chemother Pharmacol 56 Suppl 1:10-20, 2005.
Ciardiello F, Tortora G. "Epidermal growth factor receptor (EGFR) as a target in cancer therapy: understanding the role of receptor expression and other molecular determinants that could influence the response to anti-EGFR drugs," Eur J Cancer 39:1348-54, 2003.
Camp RL, Dolled-Filhart M, King BL, et al. "Quantitative Analysis of Breast Cancer Tissue Microarrays Shows That Both High and Normal Levels of HER2 Expression Are Associated with Poor Outcome," Cancer Res 63:1445-8, 2003.
Howell A, Cuzick J, Baum M, et al. "Results of the ATAC (Arimidex, Tamoxifen, Alone or in Combination) trial after completion of 5 years' adjuvant treatment for breast cancer," Lancet 365:60-2, 2005.
Punglia RS, Kuntz KM, Winer EP, et al. "The impact of tumor progesterone receptor status on optimal adjuvant endocrine therapy for postmenopausal patients with early-stage breast cancer: a decision analysis," Cancer 106:2576-82, 2006.
International Search Report issued by the International Bureau in connection with International Application No. PCT/US2008/08229.
Written Opinion of the International Searching Authority issued by the International Searching Authority (ISA/US) in connection with International Application No. PCT/US2008/08229.
Matsumoto et al. "Markers of cell proliferation and expression of melanosomal antigen in lymphangioleimyomatosis," Am. J. Respir. Cell. Mol. Biol. Sep. 1999 (19.1999), vol. 21, No. 3 pp. 372-326.
Vollmer et al. "Use of Bayes Rule and MIB-1 Proliferation Index to Discriminate Spitz Nevus From Malignant Melanoma," Am. J. Clin. Pathol. 2004, vol. 122, pp. 499-505.
Sundram et al. "Expression of the B-Cell Proliferation Marker MUM1 by Melanocytic Lesions and Comparison with S100, gp100 (HMB45), and MelanA," Mod. Pathol. 3003, vol. 16, No. 8 pp. 802-810.
International Search Report issued by the International Bureau in connection with International Application No. PCT/US2008/08007.
Written Opinion of the International Searching Authority issued by the International Searching Authority (ISA/US) in connection with International Application No. PCT/US2008/08007.
Notice of Allowance issued Aug. 20, 2010 in connection with U.S. Appl. No. 11/894,680, filed Aug. 20, 2007.
Konenen, et al. "Tissue Microarrays for High-Throughput Molecular of Tumor Specimens," Nature Medicine, Jul. 1998, vol. 4, No. 7, pp. 844-847.
Bubendorf et al. "Survey of Gene Amplifications during Prostate Cancer Progression by High-Throughput Fluorescence in Situ Hybridication on Tissue Microarrays," Cancer Research (1999) vol. 59, pp. 803-806.
Official Action issued Oct. 6, 2010, by the Japanese Patent Office in connection with Japanese Patent Application No. 2008-78 (divisional application of Japanese Patent Application No. 2002-583976, national stage of PCT International Application No. PCT/US02/12084 and english translation of same.
Arnold et al., "Molecular Determinants for Subcellular Localization PSD-95 with an Interacting K+ Channel," Neuron, May 1999, 24:149-157.
Chen et al., "Ratio-Base Decisions and the Quantitative Analysis of cDNA Microarray Images," J. Biomed. Optics, Oct. 1997, 2(4):364-374.
Forus et al., "Sensitive Fluorescent in situ Hybridisation Method for the Characterisation of Breast Cancer Cells in Bone Marrow Aspirates," The Journal of Clinical Pathology, 1999, 52:68-74.
Klein et al., "The Neuroimmune Interface in Prion Diseases," News Physiol. Sci., Oct. 2000, 15:250-255.

Rigaut et al., "Three-Dimensional DNA Image Cytometry by Confocal Scanning Laser Microscopy in Thick Tissue Blocks," Cytometry, 1991, 12:511-524.
Staines et al., "Three-Color Immunofluorescence Histochemistry Triple Labeling Within a Single Section," The Journal of Histochemistry and Cytochemistry, (1988), 36(6):145-151.
Wood et al., "B-Spectrin is Colocalized with Both Voltage-gated Sodium Channels and AnkyrinG at the Adult Rat Neuromuscular Junction," The Journal of Cell Biology, 1998, 140(3):675-684.
Zhou et al., "A Multiple Wavelength Algorithm in Color Image Analysis and Its Applications in Stain Decomposition in Microscopy Images," Med. Phys., 1996, 23(12):1977-1986.
Nov. 23, 2010 Office Action in connection with U.S. Appl. No. 11/789,361, filed Apr. 23, 2007.
Dec. 21, 2010 Office Action in connection with U.S. Appl. No. 11/820,786, filed Jun. 20, 2007.
Dec. 23, 2010 Office Action in connection with U.S. Appl. No. 11/894,297, filed Aug. 20, 2007.
Brown et al., "A Two Focal Plane Method for Digital Quantification of Nuclear Immunoreactivity in Large Brain Areas Using NIH-image Software," Brain Research Protocols, 1998, vol. 2:264-272.
Gustafsson et al. "I5M: 3D Widelight Light Microscopy with Better Than 100 nm Axial Resolution," Journal of Microscopy, 1999, vol. 195: 10-16.
International Search Report issued by the International Bureau on Dec. 6, 2010 in connection with International Application No. PCT/US10/52471.
Written Opinion of the International Searching Authority issued by the International Search Authority (ISA/US) on Dec. 6, 2010 in connection with International Application No. PCT/US10/52471.
Shah, et al., "Expression of Syndecan-1 and Expression of Epidermal Growth Factor Receptor are Associated with Survival in Patients with Nonsmall Cell Lung Carcinoma," Cancer 2004, 101(7): 1632-1638.
Wang, et al. "Identification of Genes Differentlly Over-Expressed in Lung Squamous Cell Carcinoma using Combination of cDNA Subtraction and Microarry Analysis," Oncogene 2000, 19:1519-1528.
Scagliotti, et al. "Phase III Study Comparing Cisplatin Plus with Cisplatin Plus Pemetrexed in Chemotherapy-Naïve Patients with Advanced-Stage Non-Small-Cell Lung Cancer," J Clin Oncol. Epub May 27, 2008, 26(1): 3543-51.
Official Communication Pursuant to Article 94 (3) from European Patent Office dated Oct. 14, 2010 in connection with European Patent Application No. 02739157.2 (regional stage of PCT International Application No. PCT/US02/12084).
International Search Report issued by the International Bureau in connection with International Application No. PCT/US 10/54799 on Jan. 10, 2011.
Written Opinion of the International Searching Authority issued by the International Search Authority (ISA/US) in connection with International Application No. PCT/US10/54799 on Jan. 10, 2011.
Rothberg, B.G., et al. "Melanoma Prognostic Model Using Tissue Microarrays and Genetic Algorithms" J Clin Oncol 2009; 27:5772-5780.
Slingluff, C.L. et al. "Lethal "Thin" Malignant Melanoma Identifying Patients at Risk," Ann. Surg. Aug. 1998, vol. 208(2), pp. 150-161.
Berger, A.J. et al. "Subcellular Localization of Activating Transcription Factor 2 in Melanoma Specimens Predicts Patient Survival," Cancer Research, Dec. 2003, vol. 63(23), pp. 8103-8107.
Rothberg, B.E.G et al. Melanoma Prognostic Model Using Tissue Microarrays and Genetic Algorithms. Journal of Oncology. Nov. 2, 2009, vol. 27(34), pp. 5572-5780: abstract.
European Search Report issued by the European Patent Office in connection with PCT/US2007016014 on Feb. 11, 2011 including Supplemental European Search Report and the European Search Opinion.
Edler et al. "Immunohistochemically Detected Thymidylate Synthase in Colorectal Cancer: an Independent Prognostic Factor of Survival," Clinical Cancer Research, US vol 6, No 2, Feb. 1, 2000.
McCabe et al. "Automated Quantitative Analysis (AQUA) of In Situ Protein Expression, Antibody Concentration, and Prognosis," Journal of the National Cancer Institute, vol. 97. No. 24, Dec. 2, 2005.
Psyrri Amanda et al. Quantitative Determination of Nuclear and Cytoplasmic Epidermal Growth Factor Receptor Expression in Oropharyngeal Squamous Cell Cancer by Using Automated Quantitative Analysis, Clinical Cancer Research, vol. 11(16), Aug. 15, 2005.
Feb. 23, 2009 Office Action issued in connection with U.S. Appl. No. 11/827,694, filed Jul. 13, 2007.
Fernandez-Contreras et al. "Thymidylate synthase expression pattern is prognostic factor in patients of colorectal cancer treated with 5-fluorouracil," Int'l J. Oncol., Oct. 2004, vol. 25, No. 4, pp. 887-885, abstract only.
Aug. 24, 2009 Response to Feb. 23, 2009 Office Action issued in connection with U.S. Appl. No. 11/827,694, filed Jul. 13, 2007.
Dec. 29, 2009 Office Action issued in connection with U.S. Appl. No. 12/215,458, filed Jun. 27, 2008.
Apr. 29, 2010 Response to Dec. 29, 2010 Office Action issued in connection with U.S. Appl. No. 12/215,458, filed Jun. 27, 2008.
Jul. 22, 2010 Office Action issued in connection with U.S. Appl. No. 12/215,458, filed Jun. 27, 2008.
Oct. 20, 2010 Response to Jul. 22, 2010 Office Action in connection with U.S. Appl. No. 12/215,458, filed Jun. 27, 2008.
Mar. 23, 2011 response to Nov. 23, 2010 Office Action in connection with U.S. Appl. No. 11/789,361, filed Apr. 23, 2007.
Apr. 14, 2011 response to Dec. 21, 2010 Office Action issued in connection with U.S. Appl. No. 11/820,786, filed Jun. 20, 2007.
Apr. 26, 2011 Response to Oct. 14, 2010 Official Communication in connection with European Patent Application No. 02739157.2 (national stage of PCT International Application No. PCT/US02/12084).
Mar. 7, 2011 Written Argument and Amendment to Oct. 6, 2010 Official Action in connection with Japanese Patent Application No. 2008-00078.
Notice of Allowance issued Jun. 9, 2011 in connection with U.S. Appl. No. 11/789,361, filed Apr. 23, 2007.
Jun. 23, 2011 Response to Dec. 23, 2011 Office Action issued in connection with U.S. Appl. No. 11/894,297.
Jun. 16, 2011 Office Action issued in connection with U.S. Appl. No. 11/820,786, filed Jun. 20, 2007.
Jul. 25, 2011 Official Communication purusant to Article 94(3) EPC in connection with European Application No. 02 739 157.2.
Sep. 5, 2011 Response to Communication Pursuant to Rules 70(2) and 70(a) (2) issued by the European Patent Office on Mar. 1, 2011 in connection with European Patent Application No. 07810453.6.
Sep. 8, 2011 Final Office Action issued in connection with U.S. Appl. No. 11/894,297, filed Aug. 20, 2007.
Sep. 27, 2011 Response to Jun. 16, 2011 Final Office Action issued in connectiong with U.S. Appl. No. 11/820,786, filed Jun. 20, 2007.
Nov. 29, 2011 Amendement in Response to Sep. 8, 2011 Final Office Action issued in connection with U.S. Appl. No. 11/894,297.
Official Action issued by the Japanese Patent Office on Oct. 26, 2011, in connection with Japanese Patent Application No. 2009-519548(national stage of PCT International Application No. PCT/US2007/106014, filed Jul. 13, 2007 on behalf of Yale University).
Notice of Allowance issued Oct. 14, 2011 in connection with U.S. Appl. No. 11/820,786, filed Jun. 20, 2007.
Notice of Allowance and Examiner's Amendment issued Jan. 19, in connection with U.S. Appl. No. 11/894,297, filed Aug. 20, 2007.
Feb. 6, 2012 Response to Jul. 25, 2011 Communication pursuant Article 94(3) EPC issued by the European Patent Office in connection with European Patent Application No. 02739157.2.
Apr. 5, 2012 Office Action issued in connection with U.S. Appl. No. 12/661,141, filed Mar. 10, 2012.
Apr. 24, 2012 Written Argument and Amendment filed in response to Oct. 25, 2011 Official Action issued by the Japanese Patent Office in connection with Japanese Patent Application No. 2009-529548, filed Jan. 23, 2009 (national stage of PCT International Application No. PCT/US2007/016014, filed Jul. 13, 2007) and English draft sent to Japanese associates upon which Argument and Amendment was based.
Jun. 5, 2012 Response to Office Action issued Apr. 5, 2012 in connection with U.S. Appl. No. 12/661,141.
International Search Report and Written Opinion of the International Searching Authority mailed Oct. 16, 2007 in connection with PCT/US2007/011052.
Examiner's Report Issued by Australian Patent Office on Mar. 19, 2012 in connection with Australian Patent Application No. 2007248424, national stage of PCT International Application No. PCT/US07/011052, filed May 7, 2007.
Amendment and Written Argument filed on Apr. 13, 2012 in response to Japanese Official Action mailed on Oct. 13, 2011 in connection with Japanese Application No. 2009-509783, national stage of PCT International Application No. PCT/US07/011052, filed May 7, 2007 and English translation of Amended Claims.
Communication Pursuant to Rules 161 and 162 EPC dated Jan. 8, 2009 issued by the European Patent Office in connection with European Patent Application No. 07776850.5 (national stage of PCT International Application No. PCT/US07/011052).
Response filed on Feb. 18, 2009 in response to Communication Pursuant to Rules 161 and 162 EPC dated Jan. 8, 2009 issued by the European Patent Office in connection with European Patent Application No. 07776850.5 (national stage of PCT International Application No. PCT/US07/011052).
Communication pursuant to Article 94(3) dated Aug. 10, 2009 issued by the European Patent Office in connection with European Patent Application No. 07776850.5 (national stage of PCT International Application No. PCT/US07/011052).
Response filed on Feb. 12, 2010 in response to Communication pursuant to Article 94(3) dated Jun. 10, 2009 issued by the European Patent Office in connection with European Patent Application No. 07776850.5 (national stage of PCT International Application No. PCT/US07/011052).
Communication pursuant to Article 94(3) dated Jul. 29, 2010 issued by the European Patent Office in connection with European Patent Application No. 07776850.5 (national stage of PCT International Application No. PCT/US07/011052).
Response filed on Dec. 7, 2010 in response to Communication pursuant to Article 94(3) dated Jul. 29, 2010 issued by the European Patent Office in connection with European Patent Application No. 07776850.5 (national stage of PCT International Application No. PCT/US07/011052).
Communication pursuant to Article 94(3) dated Jun. 6, 2011 issued by the European Patent Office in connection with European Patent Application No. 07776850.5 (national stage of PCT International Application No. PCT/US07/011052).
Response filed on Sep. 26, 2011 in response to Communication pursuant to Article 94(3) dated Jun. 6, 2011 issued by the European Patent Office in connection with European Patent Application No. 07776850.5 (national stage of PCT International Application No. PCT/US07/011052.
Nozawa, Nobuyoshi et al. "Immunohistochemical alpha- and beta-catenin and E-cadherin expression and their clinicopathological significance in human lung adenocarcinoma," Pathology Research and Practice 202: 639-650 (2006).
Au, NHC et al. "Evaluation of immunohistochemical markers in non-small cell lung cancer by unsupervised hierarchical clustering analysis: a tissue microarray study of 284 cases and 18 markers," J. Pathol; 204: 101-109 (2004).
Berclaz, Filles et al., "EGFR dependent expression of STAT3 (but not STAT1) in breast cancer," Int. Journal of Oncology, 19(6):1155-1160 (Dec. 2001).
Camp, Robert L., et al., "Automated subcellular localization and quantification of protein expression in tissue microarrays," Nature Medicine, 8(11):1323-1327 (Nov. 2002).
Concolini, Giuseppe, et al. "Human Renal Cell Carcinoma as a Hormone-dependent Tumor", Cancer Research 38(11) Part 2:4340-4344 (1978).
Suzuki, Shioto, et al. "Diversity of epidermal growth factor activation of downstream molecules in human lung carcinomas," Modern Pathology 19(7):986-998 (Apr. 28, 2006).
Japan Molecular Biology Academy Yearly Meeting Abstracts of Lectures 1P-1261 (2005).
Japanese Official Action mailed on Oct. 13, 2011 in connection with Japanese Application No. 2009-509783, national stage of PCT International Application No. PCT/US07/011052, filed May 7, 2007 and English translation.
Office Action issued on Jul. 12, 2012 in connection with U.S. Appl. No. 12/299,699, filed Nov. 23, 2009.
Notice of Allowance issued on Oct. 5, 2012 in connection with U.S. Appl. No. 12/299,699, filed Nov. 23, 2009.

METHODS FOR DETERMINING SIGNAL TRANSDUCTION ACTIVITY IN TUMORS

This application is a divisional of U.S. Ser. No. 12/299,699, filed Nov. 23, 2009 to be issued as U.S. Pat. No. 8,367,351 on Feb. 5, 2013, a 371 national stage application of PCT/US2007/011052, filed May 7, 2007, which claims the benefit of U.S. Provisional Application No. 60/797,932, filed May 5, 2006, the contents of each of which are hereby incorporated by reference in their entireties into this application.

BACKGROUND

Receptor tyrosine kinase signaling and other receptor mediated signaling pathways typically progress through a pathway that includes ligand binding, receptor activation, phosphorylation of signaling intermediary proteins in the cytoplasm that amplify or network the signal, translocation of a subset of the signaling proteins into the nucleus, followed by activation of transcription, by either the translocated protein or other nuclear co-factors.

EGFR (HER1) is a member of the HER family of receptor tyrosine kinases (RTKs). Each RTK has a ligand-binding domain, a single membrane-spanning region, and a cytoplasmic tyrosine-kinase-containing domain. Under normal physiological conditions, activation typically is controlled by both the temporal and spatial expression of the RTK ligands including mechanisms such as homo- or hetero-dimerization of receptors, activation of kinase domains, phosphorylation, and resulting docking-sites in modified domains that allow for activation of downstream signaling pathways involved in growth, proliferation, and/or survival such as Ras/MAPK, PI3K/Akt, PLCγ, and STAT. Dysregulation of the EGFR/HER1 signaling pathway is known to be involved in the development and growth of many tumors, including bladder, brain, breast, colon, esophagus, head, kidney, lung, ovary, neck, pancreas, prostate and stomach. (See e.g., Marmor, M. D., K. B. Skaria, and Y. Yarden. 2004. Signal transduction and oncogenesis by ErbB/HER receptors *Int. J. Radiat. Oncol. Biol. Phys.* 58:903-913; Olayioye, M. A., R. M. Neve, H. A. Lane, and N. E. Hynes. 2000. The ErbB signaling network: receptor heterodimerization in development and cancer. *EMBO J.* 19:3159-3167; Riese, D. J., and D. F. Stern. 1998. Specificity within the EGF family/ErbB receptor family signaling network. *Bioessays.* 20:41-48; Schlessinger, J. 2004. Common and distinct elements in cellular signaling via EGF and FGF receptors. *Science.* 306:1506-1507; and Yarden, Y., and M. X. Sliwkowski. 2001. Untangling the ErbB signalling network. *Nat. Rev. Mol. Cell Biol.* 2:127-137.)

The monoclonal antibody Erbitux (cetuximab), which targets EGFR, has FDA approval for the treatment of colorectal cancer. In addition, Iressa and Tarceva, two small molecules that target EGFR, have FDA approval for non small cell lung cancer. DakoCytomation California, Inc. provides an FDA approved companion diagnostic that can detect EGFR in patient biopsies. This test can be useful, for example to identify patients, who should respond favorably to EGFR targeted therapeutics. However, experience has shown that currently available EGFR diagnostic tests do not correlate well with patient response to treatment with and EGFR targeted therapeutic.

US2006/0094068 and US2007/0059785 each teach an assay for one or another of a molecular marker (which may include pERK or a total cytoplasmic ERK compared to total nuclear ERK) that may be useful in predicting if an individual will or determining if an individual patient is responding to treatment with an EGF or EGFR inhibitor. The method requires a pre and post treatment biopsy from a subject treated with an EGF or EGFR inhibitor.

There is a need for methods for determining the signal transduction pathway activation state with specific reference to the receptor of interest which likely requires that the receptor and pathway effector molecule expression levels be determined in the same assay to achieve adequate levels of accuracy.

There is also a need for methods for determining the signal transduction pathway activation state associated with a receptor that evaluates more than one possible pathway in the same assay.

There is also a need for an assay that does not require a post treatment biopsy. The lability of phosphorylated proteins, even during short ischemic times between tissue excision and fixation (or freezing) may limit the clinical utility of an assay based strictly on detection of phosphorylated proteins. Therefore there is also a need to devise alternative strategies for determining signal transduction pathway activation state without relying on accurate detection of phosphorylated effector molecules, especially for those molecules that turn out to be unstable in routine clinical practice or when suitably specific detection reagents are not available.

There is also a need for a method that can provide prognostic information based on the receptor expression and the signal transduction pathway(s) activation state.

SUMMARY OF THE INVENTION

In one aspect, the invention features an immunohistochemical assay method for measuring signal transduction pathway activity in a tissue section. In one embodiment the method includes staining the tissue section with 1) reagents to detect the cell receptor protein of interest 2) reagents to detect at least one signal transduction effector molecule and analyzing the stained section to quantitate the relative amounts of receptor protein and effector molecule. In one embodiment, two effector molecule expression levels are detected and in another embodiment, three effector molecule expression levels are detected. Furthermore by determining the ratio of effector molecule expression levels in the nucleus compared to the cytoplasm, signal transduction activity may be determined. In a particular embodiment of the invention, the cytoplasmic to nuclear expression ratio of three downstream effector molecules combined with the receptor expression level had prognostic significance.

In another aspect, the invention features kits useful for carrying out the described methods.

Analyses of tumors for the expression level of EGFR and the ratio of the amount of at least one EGFR downstream effector molecule in the nucleus to that in the cytoplasm provides an indication of the activation level of an EGFR signaling pathway in a particular tumor. This important information can be useful, for example, for: (a) prognostic classification of patients, (b) prediction of drug response, (c) selection of patients for biospecific therapies (such as, but not limited to, drugs targeting EGFR or HER-family signaling), (d) identification of responders to drugs and/or for identification of drug resistance. Quantitating multiple EGFR downstream effector molecules and averaging the nuclear/cytoplasmic ratios for each can normalize for variations (e.g., due to fixation conditions, etc.), thus providing classificatory power beyond that achievable through quantitative measurements of single markers.

Other features and advantages will be apparent based on the following Detailed Description and Claims.

DETAILED DESCRIPTION OF THE INVENTION

Definitions

For convenience, before further description of the present invention, certain terms employed in the specification, examples and appended claims are defined here.

The singular forms "a", "an", and "the" include plural references unless the context clearly dictates otherwise.

The term "antibody" as used herein is intended to include whole antibodies, e.g., of any isotype (IgG, IgA, IgM, IgE, etc), and includes fragments thereof which are also specifically reactive with a vertebrate, e.g., mammalian, protein. Antibodies can be fragmented using conventional techniques and the fragments screened for utility in the same manner as described above for whole antibodies. Thus, the term includes segments of proteolytically-cleaved or recombinantly-prepared portions of an antibody molecule that are capable of selectively reacting with a certain protein. Nonlimiting examples of such proteolytic and/or recombinant fragments include Fab, F(ab')2, Fab', Fv, and single chain antibodies (scFv) containing a V[L] and/or V[H] domain joined by a peptide linker. The scFv's may be covalently or non-covalently linked to form antibodies having two or more binding sites. The subject invention includes polyclonal, monoclonal, or other purified preparations of antibodies and recombinant antibodies. An antibody used for detection of a biomarker of the present invention may be a labeled antibody. The labeled antibody may comprise a fluorescent label for detection.

The term "biomarker" may refer to any constituent of a cell in a tissue, including for example a protein whose presence, concentration, activity, phosphorylation state, subcellular localization profile and/or translocation state may be determined. A "biomarker" may refer to a protein that is a member of the EGFR signal transduction pathway including EGFR and EGFR downstream effector molecules.

The term "cut-point" refers to the point at which the data is divided. For example, a patient population may be divided at a cut-point x into a group of high biomarker expressors ($\geq$x) and a group of low biomarker expressors ($\leq$x) (See e.g., Camp, R. L. et al., (2004) X-tile: a new bioinformatics tool for biomarker assessment and outcome-based cut-point optimization 9. *Clin. Cancer Res.* 10:7252-7259.)

"Drugs" in accordance with the methods provided herein include, inter alia, proteins, nucleic acids including DNA, RNA, RNAi, PNA, ribozymes, antibodies, small molecules, ligands, and the like, for which the drug's effect on a target signal transduction pathway is under investigation, or is known and used to determine appropriate patient populations that are predicted to respond to the drug. The term "drug" is inclusive of natural or synthetic compounds, including candidate therapeutics.

The phrase "effector molecule" refers to any molecule in a cell signaling pathway The phrase "end effector molecule" refers to any molecule in a cell signaling pathway, that is capable of translocating between the cell cytoplasm and nucleus. Preferred effector molecules include: thymoma viral protooncogene 1 (Akt1 or Akt or PKB/Akt or PKBalpha; the human protein sequence for which is provided as NCBI accession no. AAL55732), Signal transduction and activator of transcription 3 or acute phase responder factor (Stat3; the human protein sequence for which is provided as NCBI accession no. AAK17196)) and mitogen-activated protein kinase 3 (MAPK3 or Erk1; the human protein sequence for which is provided as NCBI accession no. AAH13754), Grb2, Ras, mTOR, GSK3, eIF2B, NFkB, CREB, JAK. EGFR downstream effector molecules may or may not be phosphorylated at any given time.

"EGFR or Epidermal Growth Factor Receptor" also referred to as HER1 or ErbB-1 is a cell surface receptor member of the epidermal growth factor family. The human EGFR protein is provided in NCBI Accession Nos. NP_958439 and NP_955441, the sequences of which are expressly incorporated herein by reference.

A "signaling profile" refers to the combination of a receptor expression level for a particular tumor and the expression level of at least one effector molecule. In a preferred embodiment the signaling profile is the combination of the EGFR expression level for a particular tumor and the average nuclear to cytoplasmic ratio for at least one downstream effector molecule.

An "EGFR targeted therapeutic" refers to a drug that targets EGFR in a subject, examples, include but are not limited to Erbitux (cetuximab), Iressa and Tarceva.

A "patient" or "subject" may mean either a human or non-human animal.

"Protein", "polypeptide" and "peptide" are used interchangeably herein when referring to a gene product, e.g., as may be encoded by a nucleic acid coding sequence.

"Signaling quotient" refers to the averaged nuclear:cytoplasmic ratio for at least one receptor downstream effector molecule.

"Signaling potential" refers to the relative activity of a tumor cell signal transduction pathway. Tumors with active signaling pathways are expected to be more aggressive resulting in a decreased patient survival time. Conversely, tumors with inactive signaling pathways are expected to be less aggressive resulting in an increased patient survival time.

"Small molecule" refers to a composition, which has a molecular weight of less than about 2000 kDa. Small molecules may be nucleic acids, peptides, polypeptides, peptidomimetics, carbohydrates, lipids or other organic (carbon-containing) or inorganic molecules. As those skilled in the art will appreciate, based on the present description, libraries of chemical and/or biological mixtures, often fungal, bacterial, or algal extracts, may be screened with any of the assays of the invention to identify compounds that modulate a bioactivity.

A "subcellular localization profile" refers to the level of a receptor downstream effector molecule in a subcellular location for example the cell nucleus or the cell cytoplasm. In a preferred embodiment the subcellular localization profile is the level of an end effector molecule in the nucleus compared to the level of the same effector molecule in the cytoplasm. The subcellular localization profile may be expressed in terms of a ratio (or the log of a ratio).

A "tissue sample", as used herein, refers to a biological sample obtained from a tissue in the body, for example a biopsy. In a preferred embodiment the tissue sample is of a tumor. Frequently the tissue sample will be a "clinical sample," which is a sample derived from a patient such as a fine needle biopsy sample. A "tissue sample" may also include a section of tissue such as a section taken from a frozen or fixed tumor. Tissue samples can be obtained from tumors of for example but not limited to the bladder, brain, breast, uterus, cervix, colon, rectum, esophagus, mouth, head, skin, kidney, lung, ovary, neck, pancreas, prostate, testis, liver and stomach. The tissue sample may be present on a tissue array or may comprise a whole tissue section. An "evenly matched" tissue sample is a tissue sample of the same type (i.e. comprising the same types of cells from the same type of tumor from the same type of subject). "Evenly matched" tissue samples can be used to provide reference profiles in the methods provided herein.

A "tumor" refers to an abnormal growth of tissue that may be comprised of cells that for example, express the epidermal growth factor receptor on their cellular membranes. Tumors may be present, for example, in the bladder, brain, breast, uterus, cervix, colon, rectum, esophagus, head, skin, kidney, lung (including Non Small Cell Lung Cancer), ovary, neck, pancreas, prostate, testis, liver and stomach.

General Description

The present invention is based on the finding that it is possible to assay for a receptor molecule and one or more downstream effector molecules in the receptor signal transduction pathway in tissue sections by immunohistochemical methods to determine an activation status of the pathway and to provide prognostic information. More specifically the invention pertains to an immunhistochemical method for measuring the activity of a signal transduction pathway in a tissue section including the following steps:

1) staining the tissue section with a reagent to detect a cell receptor protein; and
2) staining the tissue section with a second reagent to detect an effector molecule, the effector molecule being a member of the signal transduction pathway of the cell receptor protein;
3) using a microscope, obtaining a high resolution digital image of the stained cell receptor protein in the tissue section and of the stained effector molecule in the tissue section; and
4) analyzing the digital image to quantitate an amount of the cell receptor protein present in the tissue section and an amount of effector molecule present in the tissue section;

thereby determining the signal transduction activity in the tissue section.

A specific embodiment of the present invention is based on the surprising finding that patients with tumors that express relatively high levels of EGFR, but have a relatively low signaling quotient (i.e. higher cytoplasmic signal relative to nuclear for at least one downstream effector molecule) have the lowest survival rate. Although not wishing to be bound by theory, it is thought that tumor cells with a higher total cytoplasmic level of an effector molecule relative to the nuclear level of the effector molecule have greater signaling potential because more molecules are available for activation. In support of this hypothesis, it has been shown that nuclear accumulation of Erk1/2 is transient and nuclear Erk1/2 is quickly relocalized to the cytoplasm to await the next round of stimulation. (Adachi, M et al., (2000) Nuclear export of MAP kinase (ERK) involves a MAP kinase kinase (MEK)-dependent active transport mechanism. *J. Cell. Biol.* 148:849-856.)

Based on these findings, the invention features methods and kits for determining the signaling profile of tumors (i.e., the relative amount of receptor expressed and the signaling quotient (relative ratio of the amount of each downstream effector expressed in the nucleus over the amount expressed in the cytoplasm). A method for determining the signaling profile of a tumor comprises determining the level of receptor in a tissue sample from a tumor and at least one receptor effector molecule. In addition to quantitation of EGFR, for example, a method for determining the EGFR signaling profile of a tumor also comprises determining the nuclear and cytoplasmic levels of at least one EGFR downstream effector molecule in the tissue section. Either the phosphorylated or non-phosphorylated proteins may be measured. As an example, the levels of total downstream effector molecules in the cytoplasm may be measured, while the levels of total downstream effector molecules in the nuclear compartment may be measured. Alternatively, total p-effector molecule in the cytoplasm and total p-effector molecule in the nucleus may be measured.

The nuclear and cytoplasmic levels of the at least one EGFR downstream effector molecule in the tumor tissue are then compared to each other to determine a relative localization (cytoplasmic or nuclear) of the at least one EGFR downstream effector molecule in the subject's tumor. In one aspect, the present methods comprise determining whether Erk, AKT, Stat3, and/or other EGFR downstream effector molecule is more localized in the cytoplasm of tumor cells in the sample, or is more localized in the nucleus of tumor cells in the sample. Any suitable method of determining the relative localization of a specific biological marker may be utilized in the present methods. In one aspect, receptor levels and the nuclear and cytoplasmic levels of the at least one downstream effector molecule in the sample are specifically determined, and a ratio of the determined nuclear to cytoplasmic levels (a "nuclear to cytoplasmic ratio") is calculated to determine the relative localization and used in the context of the receptor level. In another embodiment, a "signaling quotient" may be calculated for determining the relative localization of the at least one downstream effector molecule in the sample and used in the context of the receptor level. As an example, the Signaling Quotient may be expressed as the log transformation of the average of 3 or another number of calculated ratios for nuclear:cytoplasmic levels of one or more EGFR downstream effector molecules.

The relative localization of the at least one EGFR downstream effector molecule, whether expressed as a simple ratio or Signaling Quotient or other form, is then compared to a reference from parameters determined from known patient stratification. The reference may be determined experimentally or may be a predetermined value from an already existing dataset. If the at least one EGFR downstream effector molecule in the tissue sample is determined to be localized more to the cytoplasmic compartment than the nuclear compartment, relative to a reference, and the difference in localization relative to the reference is significant, then the tumor is deemed aggressive, provided that the tumor has also been determined to have a relatively high EGFR expression level (as described above). If, however, the at least one EGFR downstream effector molecule in the tissue sample is determined to be localized more to the cytoplasmic compartment than the nuclear compartment relative to a reference, and the tumor has also been determined to have a relatively low EGFR expression level (as described above), and the difference in localization relative to the reference is significant, then the tumor is deemed as relatively less aggressive. Furthermore, if the at least one EGFR downstream effector molecule in the tissue sample is determined to be more localized to the nuclear compartment than the cytoplasmic compartment relative to a reference, and the tumor has also been determined to have a relatively low EGFR expression level (as described above), and the difference in localization relative to the reference is significant, then the tumor is deemed similarly relatively less aggressive. If the at least one EGFR downstream effector molecule in the tissue sample is determined to be more localized to the nuclear compartment than the cytoplasmic compartment relative to a reference, and the tumor has also been determined to have a relatively high EGFR expression level (as described above), and the difference in localization relative to the reference is significant, then the tumor is deemed relatively moderately to less aggressive.

EGFR and downstream effector molecules may be measured by any suitable means as is known in the art. For assessment of signal activation, the log of the signaling quotient can be used to adjust for non-normal distribution that results from construction of a ratio.

Tissue Preparation

Tissue samples are obtained from the body and include cells and extracellular matter. Tissue samples may be from humans or non human animals. Tissue samples can be from any organ and may include disease states of such organs. Tissue samples such as tumor biopsies can be obtained using known procedures, such as a needle biopsy (See Kim, C. H. et al. *J. Virol.* 66:3879-3882 (1992)); Biswas, B. et al. *Annals NY Acad. Sci.* 590:582-583 (1990)); Biswas, B. et al. *J. Clin. Microbiol.* 29:2228-2233 (1991). The tissue is to be processed in a manner that allows accurate detection and quantitation of EGFR and downstream effector proteins (e.g., Erk and AKT). The tissue sample may be prepared in a tissue microarray format and sectioned or may comprise a whole tissue section. Sections are typically prepared on microscope slides. For example, paraffin-embedded formalin-fixed specimens may be prepared, cores taken from separate areas of the specimens, each core arrayed into a recipient block, and sections cut and processed as previously described, for example, in Konenen, J. et al., Tissue microarrays for high-throughput molecular profiling of tumor specimens, (1987) *Nat. Med.* 4:844-7. When analyzing tissue samples from individuals, it may be important to prevent any changes, physiological processing or degradation, particularly in protein expression after the tissue or cells has been removed from the subject. Changes in expression levels are known to change rapidly following perturbations, e.g., heat shock or activation with lipopolysaccharide (LPS) or other reagents. In addition, the RNA and proteins in the tissue and cells may quickly become degraded. Accordingly, tissues obtained from a subject are ideally immediately fixed or frozen. Tissue specimens may also include xenograft tumor samples, particularly those from animals in drug dose ranging or toxicology studies.

Quantitation.

Any suitable method of quantitating EGFR and quantitating and localizing downstream effector molecules may be used in the present methods. One preferred method utilizes immunohistochemistry, a staining method based on immunoenzymatic reactions using monoclonal or polyclonal antibodies to detect cells or specific proteins such as tissue antigens. Typically, immunohistochemistry protocols involve at least some of the following steps: 1) antigen retrieval (eg., by pressure cooking, protease treatment, microwaving, heating in appropriate buffers, etc.); 2) application of primary antibody and washing; 3) application of labeled secondary antibody that binds to primary antibody (often a second antibody conjugate that enables the detection in step 5) and wash; 4) an amplification step may be included; 5) application of detection reagent (e.g. chromogen, fluorescently tagged molecule or any molecule having an appropriate dynamic range to achieve the level of or sensitivity required for the assay); 6) counterstaining may be used and 7) detection using a detection system that makes the presence of the proteins visible (to either the human eye or an automated analysis system), for qualitative or quantitative analyses. Various immunoenzymatic staining methods are known in the art for detecting a protein of interest. For example, immunoenzymatic interactions can be visualized using different enzymes such as peroxidase, alkaline phosphatase, or different chromogens such as DAB, AEC, or Fast Red; or fluorescent labels such as FITC, Cy3, Cy5, Cy7, Alexafluors, etc. Counterstains may include H&E, DAPI, Hoechst, so long as such stains are compatable with other detection reagents and the visualization strategy used. As known in the art, amplification reagents may be used to intensify staining signal. For example, tyramide reagents may be used. The staining methods of the present invention may be accomplished using any suitable method or system as would be apparent to one of skill in the art, including automated, semi-automated or manual systems.

The level of a receptor protein and downstream effector molecule(s) can be analyzed using an appropriate specific antibody as would be understood by one of skill in the art. Total protein level or specifically phosphorylated protein level may be determined.

The methods of the present invention may be accomplished using suitable methods or systems for analysis of immunohistochemistry, as will be apparent to one skilled in the art, including automated systems, quantitative IHC, and under some circumstances but less preferred, semi-quantitative IHC, and manual methods. As used herein, "quantitative" immunohistochemistry refers to a method, which may be automated of scanning and scoring IHC stained tissue to identify and quantitate the presence of a specified biomarker, such as an antigen or other protein. The score given to the sample may be a numerical representation of the intensity or optical density (OD) of the immunohistochemical staining of the sample, and represents the amount of target biomarker present in the sample. The quantitative measurement may be relative or absolute. For example, control specimens in the IHC assay may be correlated to ELISA results obtained for the same control specimens, thereby generating a standard curve for determining absolute concentrations of the biomarker in the tissue specimens. The score may represent the staining intensity or OD divided by unit area or percentage of cells stained. As used herein, semi-quantitative immunohistochemistry refers to scoring of immunohistochemical results for example by human eye, where a trained operator ranks results numerically (e.g., as 0, 1+, 2+ or 3+). Most preferred is quantitative immunohistochemistry that provides results on a continuous scale.

Various automated sample processing, scanning and analysis systems suitable for use with immunohistochemistry are known in the art. Such systems may include automated staining and microscopic scanning, computerized image analysis, serial section comparison (to control for variation in the orientation and size of a sample), digital report generation, and archiving and tracking of samples (such as slides on which tissue sections are placed). Cellular imaging systems are commercially available that combine conventional light, fluorescent or confocal microscopes with digital image processing systems to perform quantitative analysis on cells and tissues, including immunostained samples. See, e.g., the CAS-200 system (Becton, Dickinson & Co.); BLISS and IHCscore of Bacus Laboratories, Inc. (Lombard, Ill.); ACIS of Clarient, Inc. (San Juan Capistrano, Calif.); iVision and GenoMx of BioGenex (San Ramon, Calif.); ScanScope of Aperio Technologies (Vista, Calif.); Ariol SL-50 of Applied Imaging Corporation (San Jose, Calif.); LSC Laser Scanning Cytometer of CompuCyte Corporation (Cambridge, Mass.); and AQUA® of HistoRx Inc. (New Haven, Conn.).

In certain embodiments, the level of expression (and/or modification such as phosphorylation) of the receptor protein and downstream effector molecule biomarkers in stained tissue sections is determined using AQUA® technology, which allows quantitative measurements of protein expression within sub-cellular compartments that results, for example, in a number directly proportional to the number of molecules expressed per unit area. (see Camp, R. L., Chung, G. G. & Rimm, D. L. Automated subcellular localization and quantification of protein expression in tissue microarrays. *Nat Med* 8, 1323-7 (2002), as well as PCT/US02/12084, both of which are incorporated herein by reference in their entireties). Subcellular compartments can include morphologically defined compartments or molecularly defined compartments. A subcellular compartment may be the cell membrane, cell cytoplasm, nucleus, lysosome, ER, golgi, etc.

Methods of quantitatively determining biomarker expression may comprise determining the subcellular location of the biomarkers in the cell, as well as the quantity of total or phosphorylated protein in select subcellular compartments of the cell. AQUA® technology is an example of a method which accomplishes both of these goals. An embodiment of the methods of the invention wherein AQUA® technology is used to quantitate biomarkers in tissue is described in the Exemplification below.

Various methodologies may be used for representing the relationship between the receptor protein and the downstream effector molecules.

The signal transduction pathway activity may be represented by the relationship between the receptor protein expression level and the downstream effector molecule or molecules expression levels. This relationship may be represented by a ratio of receptor:effector, receptor to multiple effectors, individually or in combination (for example, a combination of an average, mean, median or determination based upon an optimal cutpoint, or clustal determination). Furthermore the receptor protein expression level may be related to the downstream effector molecule expression level in a particular subcellular compartment (for example receptor: effector cytoplasmic expression or receptor:effector nuclear expression). In one embodiment, the receptor protein expression level is related to the ratio of the effector expression ratio in one compartment to another, i.e cytoplasmic:nuclear ratio.

Since many receptor molecules transmit their activation signal through multiple pathways it may be desirable to combine the receptor expression level with multiple effector molecules representing one or more of the possible pathways. For example, EGFR upon ligand binding homo-dimerizes or heterodimerizes triggering tyrosine phosphorylation of the receptor sub-units. Intracellular tyrosine kinases of the Src family and Abl family are also able to tyrosine phosphorylate EGFR receptors, allowing proteins to bind through the Src homology 2 (SH2) domains leading to activation of downstream signaling cascades including 1) the RAS/ERK pathway, 2) the phosphatidylinositol 3-kinase (PI3k) pathway and 3) the Janus kinase/signal transducer and activator of transcription (JAK/STAT) pathway. The pathways are thought to act in a coordinated manner to promote cell survival, particularly in certain cancers. Therefore to determine the EGFR signal transduction activation status, an assay may include EGFR and effector molecules (total and/or phosphorylated) from the ERK pathway, the PI3k pathway and/or the JAK/STAT pathway. The ERK pathway effector molecules include Grb2, RAS, RAF1, MEK1, MEK2, ERK1 and ERK2. The PI3k pathway effector molecules include AKT, mTOR, 70s6k, eIF4B, 4E-BPI, GSK3, eIF2B, NFkB, and CREB. The JAK/STAT pathway effector molecules include JAK and STAT. (See Asnaghi L et al 2004, Pharmacol Res 50:545-549; Henson E. S., et al 2006 Cell Sig.; Jorrissen R. N. et al 2003 Exp. Cell Res. 284: 31-53; Kisseleva T. et al 2002 Gene 285:1-24; Lizcano J. M et al. 2002 Curr Bio. 12:236-238; Nair P. 2005 Curr Sci. 88:890-898; Yarden Y 2001 Eur. J. Cancer 37:S3-S8.) In a particular embodiment an EGFR signal transduction activity assay specifically measures expression of the end effector molecules for one or more of the pathways, i.e. ERK, AKT and/or STAT. As these molecules translocate from the cytoplasm to the nucleus when the pathway is active, in a particular embodiment of the present invention the cytoplasmic and nuclear levels of these end effector molecules is determined. Furthermore, in a particular embodiment an EGFR signal transduction activity assay includes determination of the ratio of cytoplasmic to nuclear AKT, ERK and/or STAT expression levels. In yet another embodiment, the cytoplasmic to nuclear effector expression ratios are averaged to provide a signaling quotient.

The present invention provides kits for practice of the afore-described methods. In certain embodiments, kits may comprise antibodies against biomarkers and appropriate reagents. Reagents may include blocking reagents, primary antibodies, secondary antibodies, amplification systems, detection reagents (chromogen, fluorophore, etc), dilution buffers, washing solutions, mounting solutions, counterstains or any combination thereof. Kit components may be packaged for either manual or partially or wholly automated practice of the foregoing methods. In other embodiments involving kits, this invention contemplates a kit including compositions of the present invention, and optionally instructions for their use. Such kits may have a variety of uses, including, for example, imaging, stratifying patient populations, diagnosis, prognosis, guiding therapeutic treatment decisions, and other applications.

The quantitation of EGFR and at least one effector molecule in the nucleus and the cytoplasm can be analyzed using an appropriate antibody. Antibodies to EGFR are commercially available, (e.g., PharmDx Kit; DAKO, Carpinteria, Calif.). Antibodies to Akt1 (e.g, mouse monoclonal, clone 2H10; Cell Signaling Technology, Danvers, Mass.) and Erk1/2 (e.g., mouse polyclonal; Cell Signaling Technology, Danvers, Mass.) are also commercially available. Antibodies specific for Ser(473)phospho-AKT are available (see, e.g., Srinivasan et al., Am J Physiol Endocrinol Metab 2002 October; 283(4):E784-93). Antibodies that react with p-erk1 and p-erk2 are commercially available (e.g., from Santa Cruz Biotechnology, Santa Cruz, Ca); see also U.S. Pat. No. 6,001, 580). Further antibodies are available from Calbiochem® (Calbiochem General Catalog, 2006-2007). Other commercial sources for appropriate antibodies are known in the art. In certain embodiments, the level of expression (and/or modification such as phosphorylation) of the biomarkers is determined by determining the AQUA® technology score of each biomarker in the panel, e.g., by using the AQUA® technology automated pathology system. AQUA® technology (for Automated Quantitative Analysis) is a method of analysis of absolute measurement of protein expression in situ. This method allows measurements of protein expression within sub-cellular compartments that results in a number directly proportional to the number of molecules expressed per unit area.

This method, including details of out-of-focus light subtraction imaging methods, is described in detail in Camp, R. L., Chung, G. G. & Rimm, D. L. Automated subcellular localization and quantification of protein expression in tissue microarrays. *Nat Med* 8, 1323-7 (2002)), as well as PCT/US02/12084, both of which reference are incorporated herein in their entireties. AQUA® is a method of analysis of absolute measurement of protein expression in situ. This method allows measurements of protein expression within sub-cellular compartments that for example results in a number directly proportional to the number of molecules expressed per unit area. Briefly, for example, to measure Akt the tissue is "masked" using an image of keratin staining obtained in one channel to determine the area of tumor and to remove the stromal and other non-tumor material from analysis. Alternatively, an image of EGFR staining may be used to generate the tumor mask. An image of DAPI staining obtained in a second channel is used in comparison to the tumor staining to define a nuclear and cytoplasmic compartment. The intensity of expression of Akt is measured by detecting the Akt staining using a third channel. The intensity of expression of a second effector molecule (for example Erk or STAT2) is measured by detecting the second effector molecule in a fourth channel. An AQUA score for a specific subcellular compartment may be generated using the intensity of that subset of pixels assigned to the compartment divided by the number of pixels. This score is directly proportional to the number of molecules of Akt per unit area of subcellular compartment in the, and may be standardized and absolute values determined using a standard curve of scores obtained for cell lines with known levels of Akt protein expression. This method is described in detail in a Nature Medicine paper (Camp, R. L., Chung, G. G. & Rimm, D. L. Automated subcellular localization and quantification of protein expression in tissue microarrays. *Nat Med* 8, 1323-7 (2002)), as well as U.S. Ser. No. 10/062,308, filed Feb. 1, 2002, which published as WO 02/086498 are incorporated by reference herein in their entireties.

An exemplary embodiment of the methods of the invention wherein AQUA® technology is used to quantitate biomarkers in tissue is described in the Exemplification below. Methods of quantitatively determining biomarker expression may comprise determining the subcellular location of the biomarkers in the cell, as well as the quantity or phosphorylated state of the biomarkers of the cell. AQUA® technology is an example of a method which accomplishes both of these goals.

EXEMPLIFICATION

The present invention is further illustrated by the following examples, which should not be construed as limiting in any way. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. (See, for example, *Molecular Cloning A Laboratory Manual, 2nd Ed.*, ed. by Sambrook, Fritsch and Maniatis (Cold Spring Harbor Laboratory Press: 1989); *DNA Cloning*, Volumes I and II (D. N. Glover ed., 1985); and *Immunochemical Methods In Cell And Molecular Biology* (Mayer and Walker, eds., Academic Press, London, 1987).

Methods for Obtaining EGFR Signaling Profiles
Materials and Methods
Tissue Microarray Design and Processing Paraffin-embedded formalin fixed specimens from 213 cases of non-small lung carcinomas (1996-2003) were obtained, as available, from the archives of the Yale University, Department of Pathology. Each tumor sample was marked for areas of invasive carcinoma, away from in situ lesions and normal epithelium, and 0.6 mm cores were taken in duplicate. Each core was arrayed into recipient blocks in a 1 mm-spaced grid, and 5-micron thick sections were cut and processed as previously described (Kononen, J. et al. 1998 Tissue microarrays for high-throughput molecular profiling of tumor specimens. *Nature Medicine.* 4, 844-847).

Immunohistochemistry

In brief, pre-cut paraffin-coated tissue microarray slides were deparaffinized and antigen-retrieved by Proteinase K (EGFR, PharmDx kit, DAKO, Carpinteria, Calif.) or pressure-cooking for 10 minutes in citrate pH 6.0 (all other primary antibodies, see below). Slides were pre-incubated with 0.3% bovine serum albumin in 0.1M tris-buffered saline (pH 8.0) (BSA/TBS) for 60 min at room temperature. Slides were then incubated with primary antibodies against EGFR (PharmDx Kit, used undiluted; DAKO, Carpinteria, Calif.), or Akt1 (mouse monoclonal, clone 2H10, diluted 1:200; Cell Signaling Technology, Danvers, Mass.) or Erk1/2 (mouse polyclonal, diluted 1:100; Cell Signaling Technology, Danvers, Mass.) or Stat3 (rabbit monoclonal, clone 124H6, diluted 1:500; Cell Signaling Technology, Danvers, Mass.) and pan-cytokeratin (either mouse or rabbit polyclonal, 1:100 dilution, DAKO, Carpinteria, Calif.) diluted in BSA/TBS overnight at 4° C. Slides were washed 3×10 min with 1×TBS containing 0.05% Tween-20. Corresponding secondary antibodies were applied for 1 h at room temperature in BSA/TBS. These included either antibodies directly conjugated to a fluorphore for anti-cytokeratin (Alexa 488-conjugated goat anti-rabbit; 1:100, Molecular Probes, Eugene, Oreg.), and/or conjugated to a horseradish peroxidase (HRP) for anti-thymidylate synthase (DAKO, Carpinteria, Calif.). Slides were again washed 3×10 min with TBS containing 0.05% Tween-20. Slides were incubated with a fluorescent chromagen (Cy-5-tyramide, NEN Life Science Products, Boston, Mass.) which, like DAB, is activated by HRP and results in the deposition of numerous covalently associated Cy-5 dyes immediately adjacent to the HRP-conjugated secondary antibody. Cy-5 (red) was used because its emission peak is well outside the green-orange spectrum of tissue autofluorescence. Slides for automated analysis were coverslipped with an antifade DAPI-containing mounting medium (ProLong Gold, Molecular Probes, Eugene, Oreg.).

Image Acquisition

Images acquisition was performed as previously described (Camp R L et al. 2002 Automated subcellular localization and quantification of protein expression in tissue microarrays. *Nature Medicine.* 8(11): 1323-1327). In brief, images of microarrays were obtained using a Deltavision platform and software (SoftWorx 2.5; Applied Precision, Issaquah, Wash.), with an attached water-cooled Photometrics series 300 camera through a ×10 Nikon Super-Fluor lens on a TE200 inverted fluorescent microscope with automated x, y, z stage movement. Low power images of microarrays were stitched together using multiple (~1500) low-resolution images of the microarray (64×64 pixel) at approximately 7-micron resolution. Specimen cores (Histospots) were identified using signal from DAPI. The coordinates of each histospot were then recorded. Subsequently, monochromatic, high-resolution (1024×1024 pixel, 0.5-micron resolution) images were obtained of each histospot, both in the plane of focus and 8 microns below it, and recorded in an image stack as bitmaps. Images were obtained using a dynamic range of 0-1024, but saved and analyzed as 8-bit tiff images with a dynamic range of 0-255.

AQUA® Analysis (RESA/PLACE Algorithms)

AQUA® analysis was performed as previously described (Camp R L et al. 2002 Automated subcellular localization and quantification of protein expression in tissue microarrays. *Nature Medicine.* 8(11): 1323-1327). In brief, a tumor-specific mask is generated by thresholding the image of a marker (cytokeratin) that differentiates tumor from surrounding stroma and/or leukocytes. This creates a binary mask (each pixel is either 'on' or 'off'. Thresholding levels were verified by spot-checking a few images and then automated for the remaining images. All subsequent image manipulations involve only image information from the masked area. Next, two images (one in-focus, one slightly deeper) are taken of the compartment-specific tags and the target marker. A percentage of the out-of-focus image is subtracted from the in-focus image, based on a pixel-by-pixel analysis of the two images. The overall degree of subtraction is based on a user-defined percentage for each subcellular compartment. For most applications this is empirically set to 40% of the total signal, and remains constant for images from an entire microarray. RESA thus eliminates all out-of-focus information. The algorithm has the added benefit of enhancing the interface between areas of higher intensity staining and adjacent areas of lower intensity staining, allowing more accurate assignment of pixels of adjacent compartments. In contrast to the compartment specific tags, the RESA subtraction of the target signal is uniform and not based on overall intensity of the image intensity. This ensures that the same amount of subtraction occurs with the target signal from all specimens. Finally, the PLACE algorithm assigns each pixel in the image to a specific subcellular compartment. Pixels that cannot be accurately assigned to a compartment to within a user-defined degree of confidence (usually 95%) are discarded. This is accomplished iteratively by determining the ratio of signal from two compartment-specific markers that minimizes the spillover of marker from one compartment into another. Pixels where the nuclear and membrane pixel intensities are too similar to be accurately assigned are negated (usually comprising <8% of the total pixels). A third compartment (the cytoplasm) can be defined by exclusion (non-membrane, non-nuclear). Once each pixel is assigned to a subcellular compartment (or excluded as described above), the signal in each location is added up. This data is saved and can subsequently be expressed either as a percentage of total signal or as the average signal intensity per compartment area. The score is expressed on a scale of 1 to 1000.

Data Analysis

Histospot containing <10% tumor, as by mask area (automated), were excluded from further analysis. Our previous studies have demonstrated that scores from the average of two histospots matches the score from an entire tissue section >95% of the time (Camp, R L et al. 2002 Validation of tissue microarray technology in breast carcinoma. *Lab. Invest.* 80:1943-1949). Each patient tumor is represented by two independent tissue cores for these analyses, and, subsequently, AQUA® scores were averaged for each patient. Furthermore, regression analysis was performed for each marker examined as a metric for experimental reproducibility as well as expression heterogeneity with Pearson R values <0.4 considering experimental error, from 0.4 to 0.7 considered heterogeneous expression, and >0.7 considered homogenous expression. Pearson R-values for each biomarker are as follows: EGFR, 0.78; Akt1, 0.44; Erk1/2, 0.55, and Stat3, 0.69. For independent survival analysis, optimal cutpoints were selected using X-Tile™ as described previously (Camp, R L et al. 2004, X-tile: a new bio-informatics tool for biomarker assessment and outcome-based cut-point optimization. *Clinical Cancer Research* 10(20:7252-7259). Monte-carlo simulations were employed since Mantel-Cox log-rank scoring is not of sufficient statistical rigor for optimal cutpoint selection. For additional statistical rigor, optimal cutpoints were determined on ⅓ of the cohort (training set) and applied to the other ⅔ of the cohort (validation set). Unsupervised and supervised hierarchical clustering analysis was performed using Cluster Software and viewed using TreeView Software for visualization of clusters (Eisen Laboratory at Stanford University). Subsequent survival analysis was performed using SPSS v14.01 (SPSS, Inc., Chicago, Ill.) and R (GNU, Boston, Mass.).

Results

Survival Analysis

Figure 1:
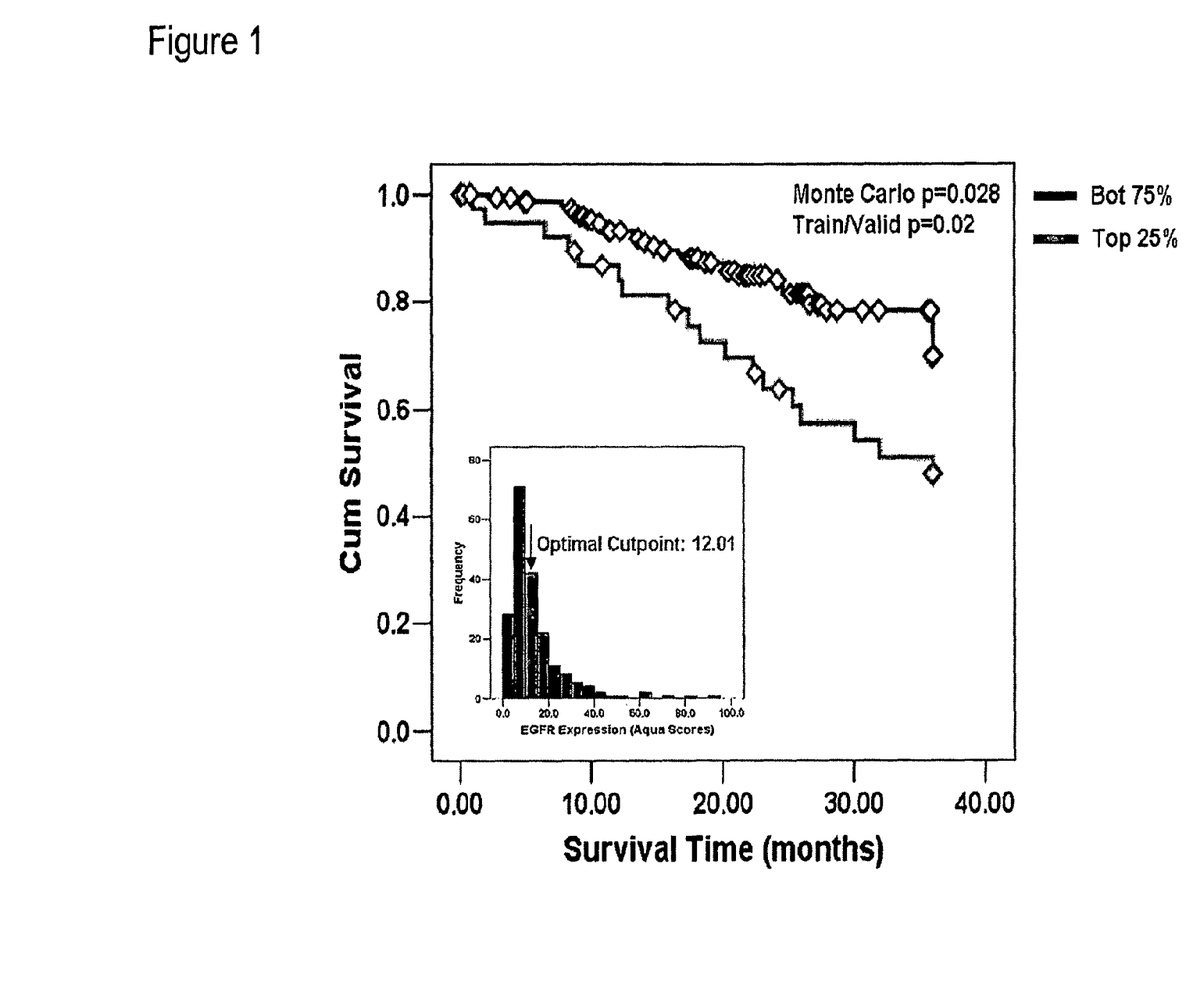
FIG. 1 is a graph plotting the cumulative survival against survival time (in months).

Examination of EGFR expression by AQUA® analysis revealed the top 25% of EGFR expressing NSCLC tumors (equivalent to a relative AQUA® score of 12; see histogram (inset, FIG. 1)) to have a statistically significant 25% decrease in three-year disease-specific survival (FIG. 1).

AQUA® analysis of key downstream signaling effectors for the EGFR pathway: Akt1, Erk1/2, and Stat3 revealed that total expression of Erk1/2 and Stat3, but not Ala1, had a significant effect on decreased overall survival (data not shown).

AQUA® analysis was used to quantitatively assess expression between sub-cellular compartments, in particular the ratio of nuclear:cytoplasmic expression for each marker. The ratios of each marker, individually did not correlate with survival. It was expected that the ratio of nuclear:cytoplasmic expression for effector molecules Akt1, Erk1/2 and Stat3 would indicate that particular pathway was active.

Hierarchical Clustering

Figure 2:
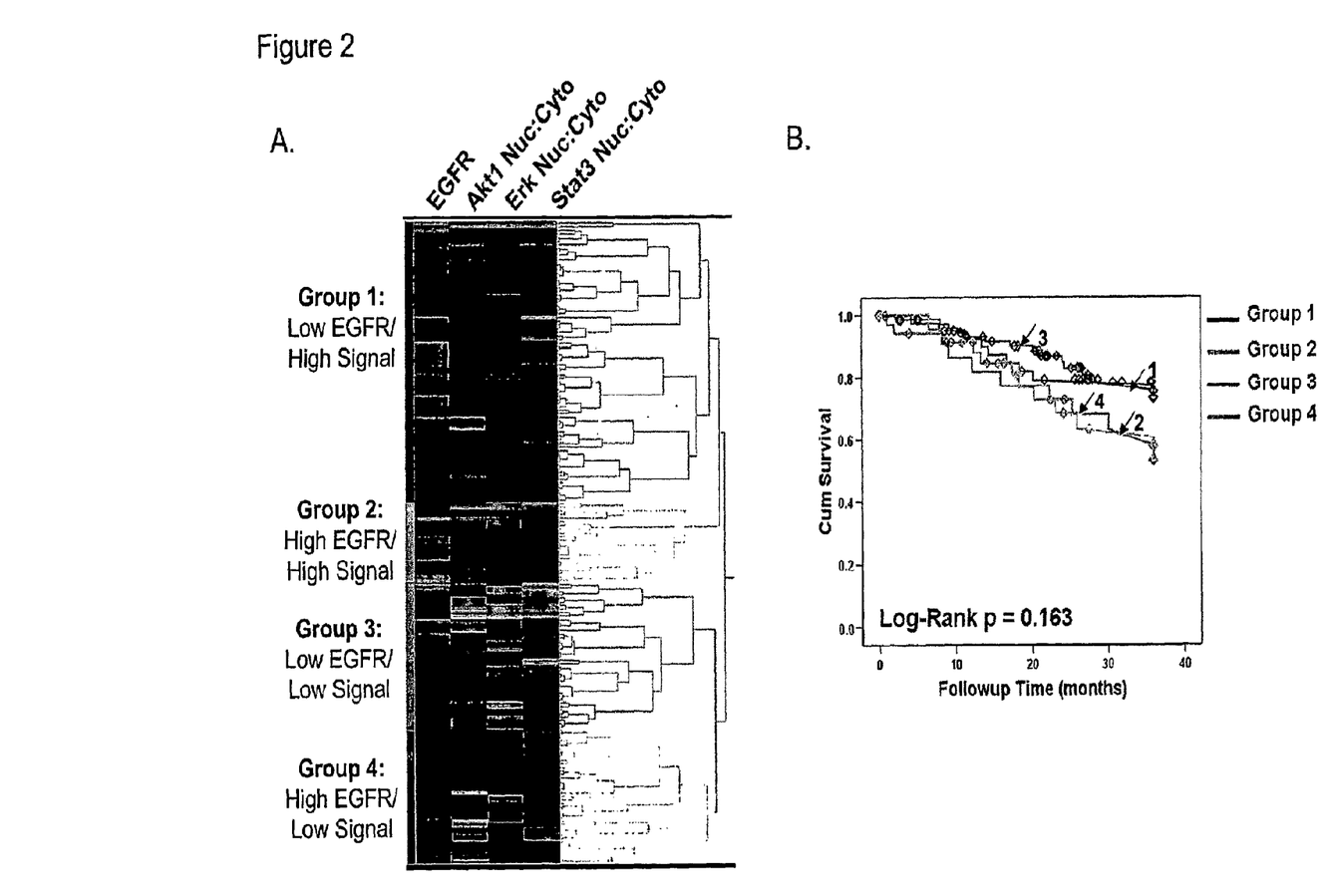
FIG. 2A plots the results of a supervised hierarchical clustering analysis performed by grouping specimens by mean AQUA® technology score for EGFR and mean Signaling Quotient (SQ) for Akt1, Erk1/2 and Stat3. Four key groups of tumors were observed.
In FIG. 2B, the Kaplan-Meier survival plot demonstrates that there was not a significant difference in survival between these 4 groups.

To assess the predictive power of individual downstream effectors as a function of the upstream receptor EGFR, a supervised hierarchical clustering analysis was performed by grouping specimens by EGFR expression and investigating trends with respect to the nuclear:cytoplasmic ratios of the key downstream effectors: Akt1, Erk1/2, and Stat3. As demonstrated in FIG. 2A, four key groups of tumors were observed (FIG. 2A). Group 1 tumors had low EGFR expression with high nuclear:cytoplasmic ratios of downstream effectors. Group 2 had high EGFR expression with high nuclear:cytoplasmic ratios. Group 3 tumors had low EGFR expression with low nuclear:cytoplasmic ratios and Group 4 had high EGFR expression with low nuclear:cytoplasmic ratios. Kaplan-Meier survival analysis demonstrated that there was not a significant difference in survival between these groups (FIG. 2B).

Signaling Quotient

Figure 3:
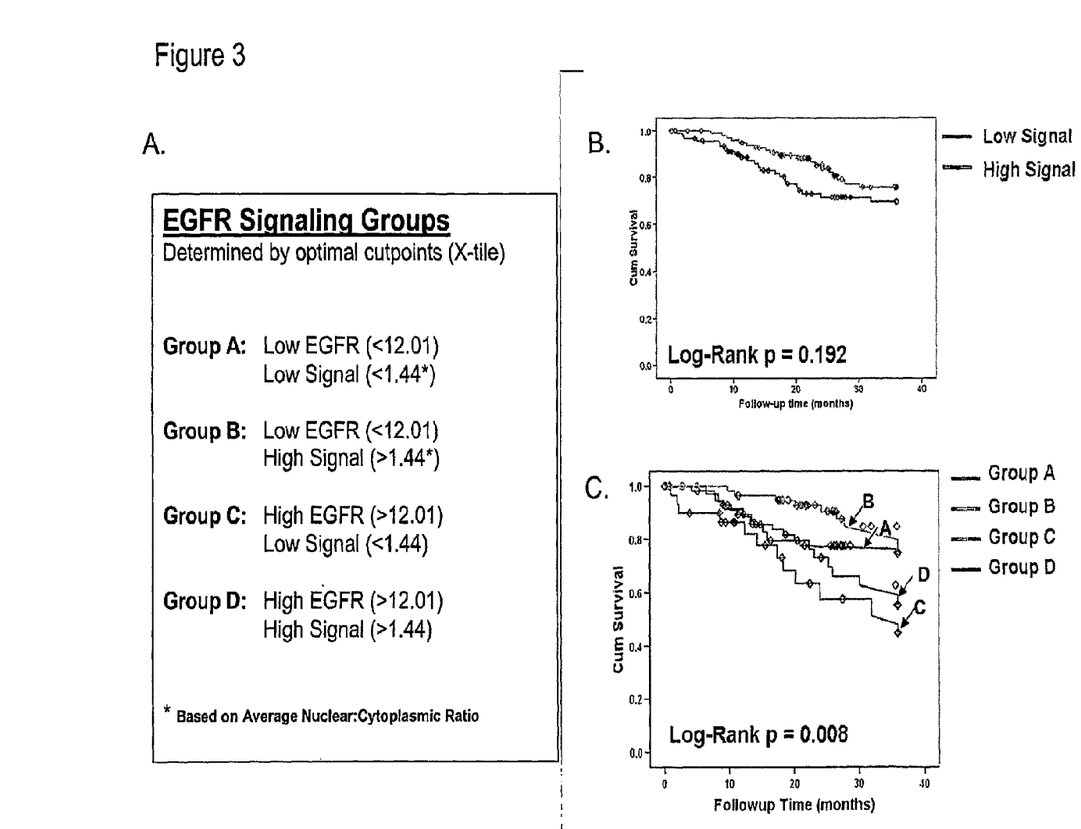
FIG. 3A shows the survival analysis split by optimal cut-point by X-tile for EGFR expression and the average nuclear:cytoplasmic ratios (a more rigorous grouping than shown in FIG. 2 above).
FIG. 3B indicates that the SQ alone does not significantly correlate with overall survival.
FIG. 3C, however, demonstrates that combining EGFR expression with the SQ resulted in significant (p=0.008) observed differences in three-year disease specific survival between all four groups.
Figure 4:
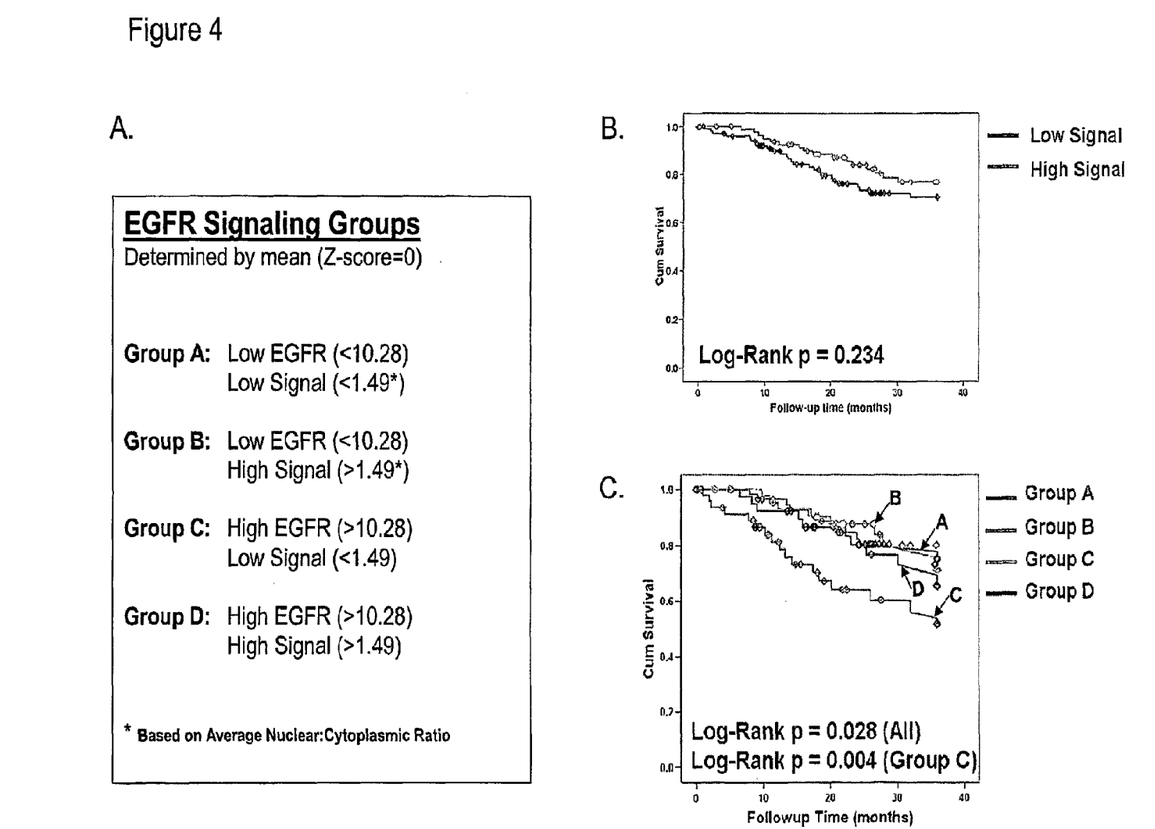
FIG. 4A shows the survival analysis split by the mean score (Z-score=0) for EGFR expression and the average nuclear:cytoplasmic ratios. Patients with high EGFR and low signaling quotient have the worst prognosis.
FIG. 4B indicates that the SQ alone does not significantly correlate with overall survival.
FIG. 4C, however, demonstrates that combining EGFR expression with the SQ resulted in significant (p=0.028) observed differences in three-year disease specific survival between all four groups. Groups A-D are distinct from those shown in FIG. 3.
Figure 5:
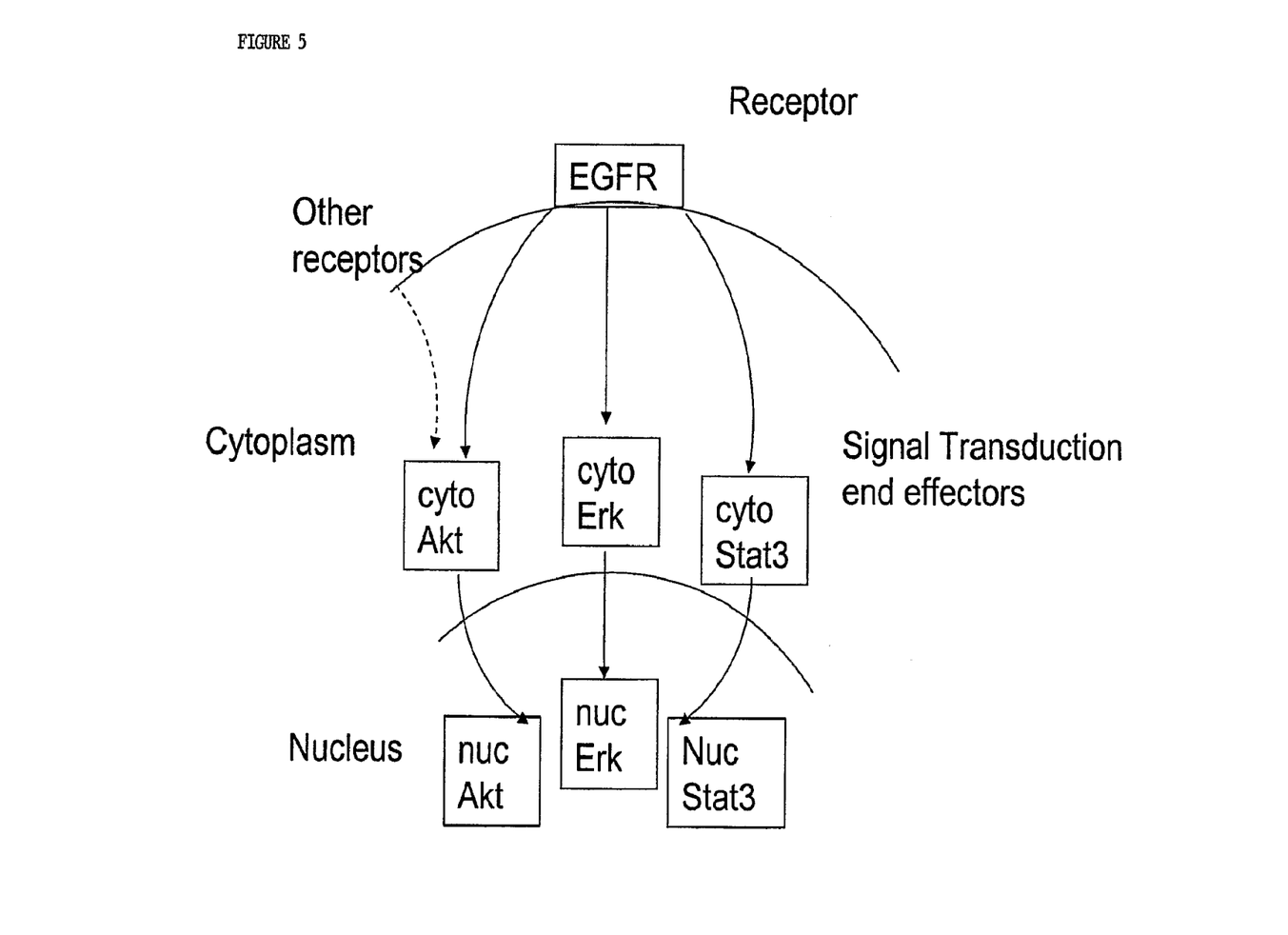
FIG. 5 schematically depicts EGFR on the membrane of the cell and the downstream effectors Akt, Erk, and Stat3 in the cytoplasm and nucleus.

The 4 groups observed with the hierarchical clustering analysis prompted an analysis based on more strict groupings based on two parameters: 1.) the optimal cutpoints (FIG. 3A) and 2.) the mean (Z-score=0; FIG. 4A) cutpoints for EGFR expression and the average nuclear:cytoplasmic ratios of the downstream effector molecules (termed "signaling quotient"). FIGS. 3B and 4B demonstrate that the signaling quotient alone does not significantly correlate with overall survival. However, combining EGFR expression with the signaling quotient resulted in significant (FIG. 3C; p=0.008) observed differences in three-year disease specific survival between all four groups based on optimal cutpoint analysis with the group representing high EGFR with a low "signaling quotient" (Group C) having the lowest overall survival. In another analysis in which the mean was used as the cutpoint (FIG. 4C), there was a significant overall difference in survival between groups (p=0.028), and Group C (high EGFR, low signaling quotient) demonstrated a more highly significant correlation with decreased overall survival as compared to the other groups (p=0.004).

REFERENCES

Incorporated by reference in their entirety are accession numbers from the public database of the National Center for Biotechnology Information (NCBI) on the world wide web at ncbi.nlm.nih.gov, which correspond to any polynucleotide or polypeptide sequences referred to herein. The contents of all cited references, as cited throughout this application, are hereby expressly incorporated by reference.

We claim:

1. A method for determining an EGFR signaling profile of a tissue section, comprising the steps of:
    (a) staining the tissue section with:
        (i) a reagent which detects EGFR;
        (ii) a second reagent which detects an EGFR effector molecule; and
        (iii) a third reagent which detects a subcellular compartment;
    (b) obtaining a high resolution digital image of:
        (i) the EGFR;
        (ii) the EGFR effector molecule; and
        (iii) the subcellular compartment; and
    (c) analyzing the digital image so obtained to obtain an amount of:
        (i) the EGFR;
        (ii) the EGFR effector molecule present in the subcellular compartment; and
        (iii) the EGFR effector molecule present outside the subcellular compartment;
    (d) determining a ratio of the amount obtained in step c(ii) to the amount obtained in step c(iii);
    (e) comparing the EGFR amount obtained in step c(i) to an expression level of EGFR in a control specimen;
    (f) comparing the ratio determined in step (d) to a corresponding ratio obtained for the control specimen;
thereby determining the EGFR signaling profile.

2. The method of claim 1 wherein the subcellular compartment is the nucleus and the area present outside the subcellular compartment comprises the cytoplasm.

3. The method of claim 2, wherein the EGFR effector molecule is selected from the group consisting of: Akt1, Erk and Stat3.

4. A method of determining the prognostic status of an EGFR expressing tumor comprising
    (a) staining the tissue section with:
        (i) a reagent which detects EGFR;
        (ii) a second reagent which detects an EGFR effector molecule; and
        (iii) a third reagent which detects a subcellular compartment;
    (b) obtaining a high resolution digital image of:
        (i) the EGFR;
        (ii) the EGFR effector molecule; and
        (iii) the subcellular compartment; and
    (c) analyzing the digital image so obtained to obtain an amount of:
        (i) the EGFR;
        (ii) the EGFR effector molecule present in the subcellular compartment; and
        (iii) the EGFR effector molecule present outside the subcellular compartment;
    (d) determining a ratio of the amount obtained in step c(ii) to the amount obtained in step c(iii);
    (e) comparing the EGFR amount obtained in step c(i) to an expression level of EGFR in a control specimen;
    (f) comparing the ratio determined in step (d) to a corresponding ratio obtained for the control specimen;
wherein (i) a tumor with an elevated level of EGFR and a lower than control effector ratio indicates a poor prognosis; (ii) a tumor with an elevated level of EGFR and a higher than control effector ratio indicates a better prognosis; (iii) a tumor with a decreased level of EGFR and a lower than control effector ratio indicates a good prognosis.

5. The method of claim 1, wherein the effector molecule is an end effector.

6. The method of claim 1, wherein the staining in step a) is by a immunohistochemical method.

7. The method of claim 1, wherein the high resolution digital image in step b) is obtained with a microscope.

8. The method of claim 7, wherein the microscope is an optical microscope.

9. The method of claim 1, wherein the effector molecule is selected from the group consisting of Grb2, Ras, ERK1, ERK2, RAF1, MEK1, MEK2, AKT, pAKT, GSK3, pGSK3, MtOR, 70s6k, eIF4B, 4E-BPI, eIF2B, NFkB, CREB, JAK, and STAT.

10. The method of claim 1, wherein the second reagent is used to determine a total effector molecule expression amount.

11. The method of claim 1, wherein the second reagent is used to determine a phosphorylated effector molecule expression amount.

12. The method of claim 1, wherein the tissue section is fixed.

* * * * *